US010316167B2

(12) United States Patent
Li et al.

(10) Patent No.: US 10,316,167 B2
(45) Date of Patent: Jun. 11, 2019

(54) OXYGEN SCAVENGERS, COMPOSITIONS COMPRISING THE SCAVENGERS, AND ARTICLES MADE FROM THE COMPOSITIONS

(71) Applicant: Plastipak Packaging, Inc., Plymouth, MI (US)

(72) Inventors: Shenshen Li, Park Ridge, IL (US); Matthew J. Dauzvardis, Manhattan, IL (US)

(73) Assignee: Plastipak Packaging, Plymouth, MI (US)

( * ) Notice: Subject to any disclaimer, the term of this patent is extended or adjusted under 35 U.S.C. 154(b) by 937 days.

(21) Appl. No.: 14/491,846

(22) Filed: Sep. 19, 2014

(65) Prior Publication Data

US 2016/0083558 A1 Mar. 24, 2016

(51) Int. Cl.

| C08K 5/17 | (2006.01) |
|---|---|
| C07D 221/06 | (2006.01) |
| C07D 209/08 | (2006.01) |
| C07D 257/10 | (2006.01) |
| C09K 15/30 | (2006.01) |
| C09K 15/18 | (2006.01) |
| B65B 5/04 | (2006.01) |

(52) U.S. Cl.
CPC .............. C08K 5/17 (2013.01); B65B 5/04 (2013.01); C07D 209/08 (2013.01); C07D 221/06 (2013.01); C07D 257/10 (2013.01); C09K 15/18 (2013.01); C09K 15/30 (2013.01)

(58) Field of Classification Search
CPC .................................... C09K 5/17; C08K 5/17
USPC ...................................................... 428/36.92
See application file for complete search history.

(56) References Cited

U.S. PATENT DOCUMENTS

| 5,021,515 | A | 6/1991 | Cochran et al. |
|---|---|---|---|
| 6,162,806 | A | 12/2000 | Arai et al. |
| 7,994,245 | B2 | 8/2011 | Deshpande et al. |
| 8,431,721 | B2 | 4/2013 | Deshpande et al. |
| 8,847,000 | B2 * | 9/2014 | Nakamura ............... A62D 3/33 252/188.1 |
| 2002/0119388 | A1 * | 8/2002 | Kobayashi ........... G03G 5/0525 430/133 |
| 2006/0069197 | A1 | 3/2006 | Tammaji et al. |
| 2007/0025908 | A1 * | 2/2007 | Sandrock .............. C01B 3/0026 423/644 |

(Continued)

FOREIGN PATENT DOCUMENTS

| JP | 2009204971 A | * | 9/2009 |
|---|---|---|---|
| JP | 2015028581 A | * | 2/2015 |

OTHER PUBLICATIONS

International Search Report and Written Opinion of the International Searching Authority for application PCT/US15/050936, filed on Sep. 18, 2015 and published as WO 2016/044722 dated Mar. 24, 2016 (Applicant—Plastipak Packaging, Inc. // Inventor—Li, et al.) (13 pages).

Primary Examiner — Michael M Dollinger
(74) Attorney, Agent, or Firm — Ballard Spahr LLP

(57) ABSTRACT

The disclosure relates to oxygen scavenging molecules, compositions, methods of making the compositions, articles prepared from the compositions, and methods of making the articles. This abstract is intended as a scanning tool for purposes of searching in the particular art and is not intended to be limiting of the present invention.

18 Claims, 4 Drawing Sheets

(56) References Cited

U.S. PATENT DOCUMENTS

| | | | |
|---|---|---|---|
| 2007/0059039 A1* | 3/2007 | Shimoyama | G03G 5/0651 399/159 |
| 2007/0141490 A1* | 6/2007 | Wu | G03G 5/0629 430/59.1 |
| 2008/0305426 A1* | 12/2008 | Kurimoto | G03G 5/047 430/125.5 |
| 2009/0092915 A1* | 4/2009 | Wu | G03G 5/047 430/58.75 |
| 2009/0104552 A1* | 4/2009 | Abe | G03G 5/0517 430/58.15 |
| 2010/0150608 A1* | 6/2010 | Mitsumori | G03G 5/0564 399/159 |
| 2010/0290807 A1* | 11/2010 | Shimoyama | G03G 5/0614 399/159 |
| 2011/0171405 A1 | 7/2011 | Deshpande | |
| 2011/0172335 A1 | 7/2011 | Deshpande | |
| 2013/0231422 A1 | 9/2013 | Deshpande | |
| 2014/0027339 A1 | 1/2014 | Deshpande et al. | |
| 2014/0228524 A1 | 8/2014 | Deshpande | |

* cited by examiner

OXYGEN SCAVENGERS, COMPOSITIONS COMPRISING THE SCAVENGERS, AND ARTICLES MADE FROM THE COMPOSITIONS

BACKGROUND

Many polymers used in packaging materials and other articles are permeable to oxygen. When oxygen permeates a polymeric composition or article, it can cause oxidative damage to the contents of the package. It is therefore desirable for certain polymer compositions and articles to have oxygen scavenging capability, such that when oxygen permeates the composition or article, oxidative damage can be mitigated.

It is known in the art to include an oxygen scavenger in the packaging structure for the protection of oxygen sensitive materials. Such scavengers are believed to react with oxygen that is trapped in the package or that permeates from outside of the package, thus extending to life of package contents. These packages include films, bottles, containers, and the like. Food, beverages (such as beer and fruit juices), cosmetics, medicines, and the like are particularly sensitive to oxygen exposure and require high barrier properties to oxygen to preserve the freshness of the package contents and avoid changes in flavor, texture and color.

Therefore, a need exists for compounds and compositions having improved oxygen scavenging capacity. These needs and other needs are satisfied by the present invention.

SUMMARY

In accordance with the purpose(s) of the invention, as embodied and broadly described herein, the invention, in one aspect, relates to oxygen scavenger molecules and compounds, compositions comprising the molecules and compounds, and articles prepared from the compositions.

Also disclosed are polymer compositions comprising the disclosed oxygen scavenging molecules.

Also disclosed are articles prepared from the disclosed compounds and compositions.

Also disclosed are methods of making oxygen scavenging molecules and polymer compositions comprising the disclosed oxygen scavenging molecules.

Also disclosed are methods for making articles comprising the disclosed compounds and compositions.

Also disclosed are methods for packaging an oxygen sensitive material using the disclosed compounds and compositions.

Also disclosed are the products and articles of the disclosed methods.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Figure 1:
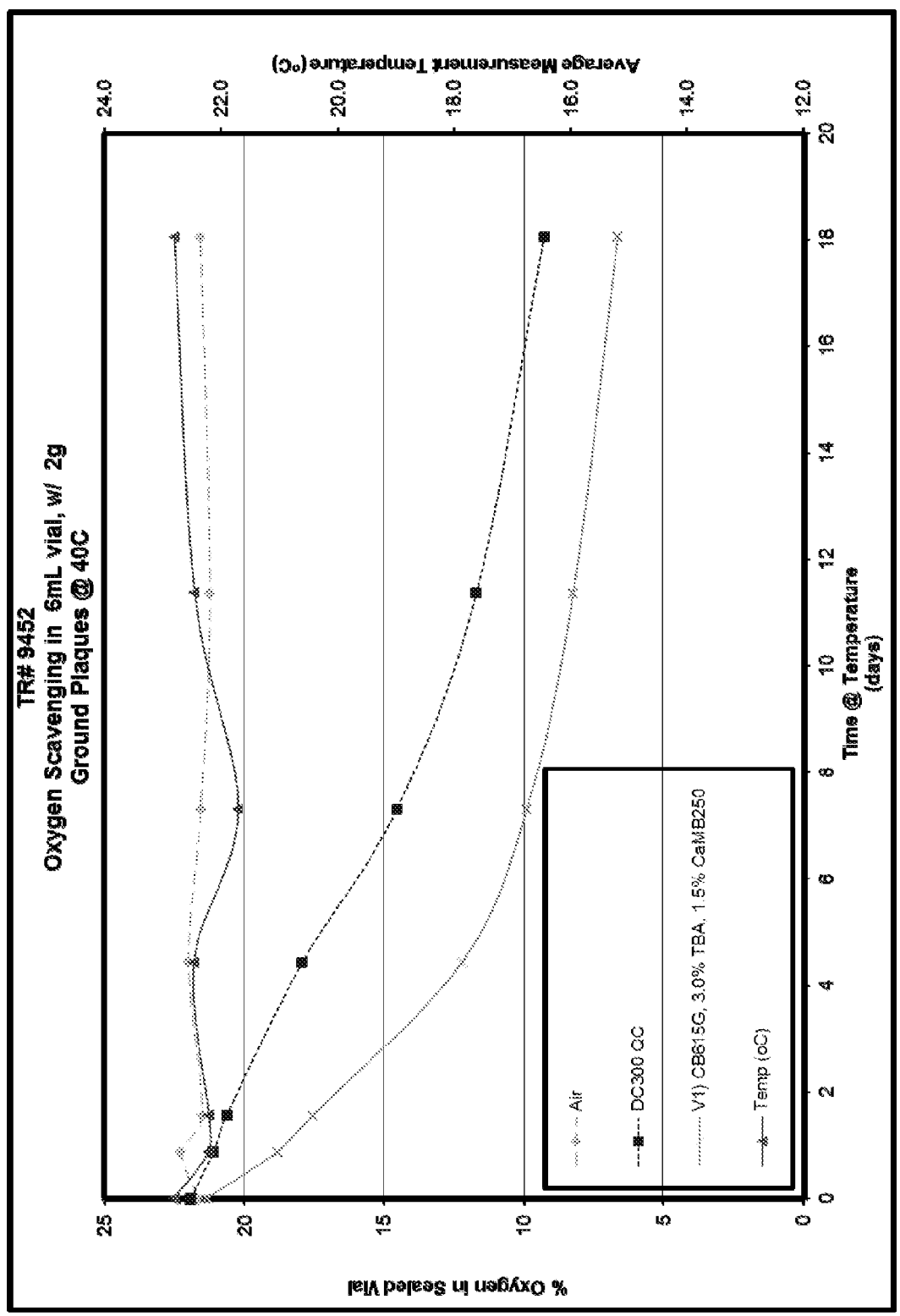
FIG. 1 shows a graph depicting oxygen scavenging data at 40° C. for plaques comprising a representative oxygen scavenger according to the present invention.

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including steps in methods of making and using the compositions of the invention. Thus, if there are a variety of additional steps that can be performed it is understood that each of these additional steps can be performed with any specific embodiment or combination of embodiments of the methods of the invention.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

Throughout the description and claims of this specification the word "comprise" and other forms of the word, such as "comprising" and "comprises," means including but not limited to, and is not intended to exclude, for example, other additives, components, integers, or steps.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance may or may not occur, and that the description includes instances where said event or circumstance occurs and instances where it does not.

As used herein, the term "substantially" means that the subsequently described event or circumstance completely occurs or that the subsequently described event or circumstance generally, typically, or approximately occurs. For example, when the specification discloses that substantially all of an agent is released, a person skilled in the relevant art would readily understand that the agent need not be completely released. Rather, this term conveys to a person skilled in the relevant art that the agent need only be released to an extent that an effective amount is no longer unreleased.

As used herein, the term "polymer" refers to a relatively high molecular weight organic compound, natural or synthetic, whose structure can be represented by a repeated small unit, the monomer (e.g., polyethylene, rubber, cellulose). Synthetic polymers are typically formed by addition or condensation polymerization of monomers.

As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers.

As used herein, the term "oligomer" refers to a relatively low molecular weight polymer in which the number of repeating units is between two and ten, for example, from two to eight, from two to six, or from two to four. In one aspect, a collection of oligomers can have an average number of repeating units of from about two to about ten, for example, from about two to about eight, from about two to about six, or from about two to about four.

As used herein, the term "molecular weight" (MW) refers to the mass of one molecule of that substance, relative to the unified atomic mass unit u (equal to 1/12 the mass of one atom of carbon-12).

As used herein, the term "number average molecular weight" ($M_n$) refers to the common, mean, average of the molecular weights of the individual polymers. $M_n$ can be determined by measuring the molecular weight of n polymer molecules, summing the weights, and dividing by n. $M_n$ is calculated by:

$$\overline{M}_n = \frac{\sum_i N_i M_i}{\sum_i N_i},$$

wherein $N_i$ is the number of molecules of molecular weight $M_i$. The number average molecular weight of a polymer can be determined by gel permeation chromatography, viscometry (Mark-Houwink equation), light scattering, analytical ultracentrifugation, vapor pressure osmometry, end-group titration, and colligative properties.

As used herein, the term "weight average molecular weight" ($M_w$) refers to an alternative measure of the molecular weight of a polymer. $M_w$ is calculated by:

$$\overline{M}_w = \frac{\sum_i N_i M_i^2}{\sum_i N_i M_i},$$

wherein $N_i$ is the number of molecules of molecular weight $M_i$. Intuitively, if the weight average molecular weight is w, and a random monomer is selected, then the polymer it belongs to will have a weight of w on average. The weight average molecular weight can be determined by light scattering, small angle neutron scattering (SANS), X-ray scattering, and sedimentation velocity.

As used herein, the terms "polydispersity" and "polydispersity index" (PDI) refer to the ratio of the weight average to the number average ($M_w/M_n$).

As used herein, the term "compatibilizing agent" refers to a small molecule or polymer that has both polar and non-polar functional groups. For example, a fatty-acid ester has both polar and non-polar functional groups.

A weight percent (wt. %) of a component, unless specifically stated to the contrary, is based on the total weight of the formulation or composition in which the component is included.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

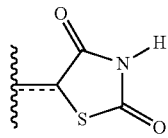

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

In some aspects, a structure of a compound can be represented by a formula:

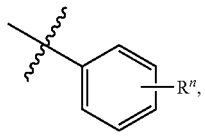

which is understood to be equivalent to a formula:

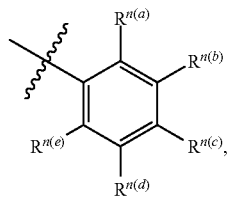

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of from 1 to 24 carbon atoms, for example from 1 to 12 carbons, from 1 to 8 carbons, from 1 to 6 carbons, or from 1 to 4 carbons, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including optionally substituted alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bond. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula NA$^1$A$^2$A$^3$, where A$^1$, A$^2$, and A$^3$ can be, independently, hydrogen or optionally substituted alkyl, cycloalkyl, alkenyl, cycloalkenyl, alkynyl, cycloalkynyl, aryl, or heteroaryl group as described herein.

The term "carboxylic acid" as used herein is represented by the formula —C(O)OH.

The term "ester" as used herein is represented by the formula —OC(O)A$^1$ or —C(O)OA$^1$, where A$^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula A$^1$C(O)A$^2$, where A$^1$ and A$^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "thiol" as used herein is represented by the formula —SH.

The terms "electron-withdrawing" or "electron-donating" as used herein refers to the ability of a substituent to withdraw or donate electrons relative to that of hydrogen if hydrogen occupied the same position in the molecule. These terms are well-understood by one skilled in the art and are discussed, for example, in Advanced Organic Chemistry by J. March, 1985, pp. 16-18. Electron withdrawing groups can include fluoro, chloro, bromo, nitro, acyl, cyano, carboxyl, lower alkenyl, lower alkynyl, carboxaldehyde, carboxyamido, aryl, quaternary ammonium, trifluoro-methyl, alkoxycarbonyl, aryloxycarbonyl, aminocarbonyl, sulfonic, alkanesulfonyl, arylsulfonyl, perfluoroalkanesulfonyl, perfluoroarylsulfonyl, phosphoryl, tertiary amine cation and a combination thereof among others. Electron donating groups can include such groups as hydroxy, lower alkoxy, lower alkyl, amino, lower alkylamino, di(lower alkyl)amino, aryloxy, mercapto, lower alkylthio, lower alkylmercapto and disulfide among others. One skilled in the art will appreciate that the aforesaid substituents may have electron donating or electron withdrawing properties under different chemical conditions.

Certain instances of the above defined terms may occur more than once in the structural formulae, and upon such occurrence each term shall be defined independently of the other.

As used herein, the term "effective amount" refers to an amount that is sufficient to achieve the desired result or to have an effect on an undesired condition. For example, a "visually effective amount" refers to an amount that is sufficient to achieve the desired result (i.e., impart color to a composition or an article), but is generally insufficient to cause adverse side affects (e.g., warping of a polymeric article).

The term "leaving group" refers to an atom (or a group of atoms) with electron withdrawing ability that can be displaced as a stable species, taking with it the bonding electrons. Examples of suitable leaving groups include sulfonate esters, including triflate, mesylate, tosylate, brosylate, and halides.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

B. Compounds and Compositions

1. Oxygen Scavengers

In various aspects, the present invention relates to oxygen scavenging compounds. In one aspect, the disclosed oxygen scavenging compounds comprise at least one aryl group attached to a heteroatom. In a further aspect, at least one of the methylene positions of the aryl group has no substitutions. In a still further aspect, the disclosed oxygen scavenging compounds is an amine-based compound. The oxygen scavenging ability of the disclosed compounds can be enhanced, in various aspects, by the presence of a transition metal. In some aspects, the disclosed oxygen scavenging compounds can be polymeric. In other aspects, the oxygen scavenging compounds can be nonpolymeric.

In one aspect, the disclosed oxygen scavenging compounds can have the general structure shown below:

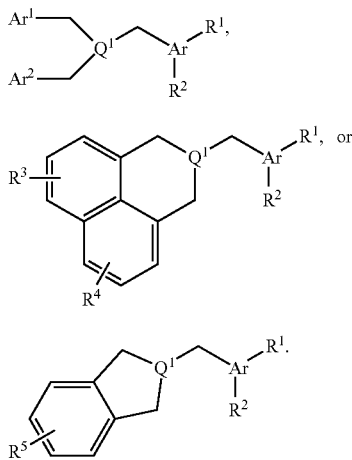

In a further aspect, each Ar is aryl or heteroaryl; each $Q^1$ is independently N or P; each of $Ar^1$ and $Ar^2$ is independently aryl or heteroaryl; each $Ar^1$ and $Ar^2$ is independently substituted with 0, 1, 2, or 3 groups independently selected from halogen, C1-C4 alkyl, and electron withdrawing groups, and valence is satisfied; each of $R^1$ and $R^2$ is independently selected from hydrogen,

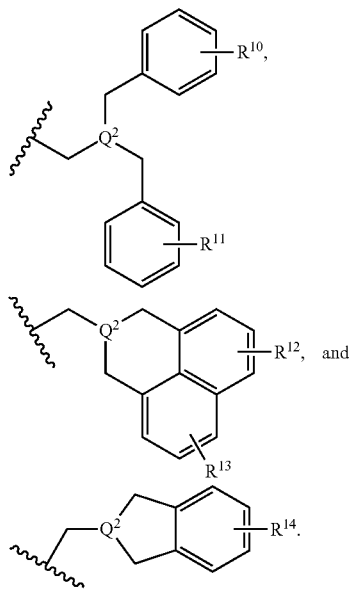

In a still further aspect, each $R^3$ represents three groups, each group independently selected from hydrogen, halogen, C1-C4 alkyl, and electron withdrawing groups; $R^4$ represents three groups, each group independently selected from hydrogen, halogen, C1-C4 alkyl, and electron withdrawing groups; $R^5$ represents four groups, each group independently selected from hydrogen, halogen, C1-C4 alkyl, and electron withdrawing groups; $R^{10}$ represents five groups independently selected from hydrogen, halogen, C1-C4 alkyl, and electron withdrawing groups; $R^{11}$ represents five groups independently selected from hydrogen, halogen, C1-C4 alkyl, and electron withdrawing groups; $R^{12}$ represents three groups independently selected from hydrogen, halogen, C1-C4 alkyl, and electron withdrawing groups; $R^{13}$ represents three groups independently selected from hydrogen, halogen, C1-C4 alkyl, and electron withdrawing groups; $R^{14}$ represents four groups independently selected from hydrogen, halogen, C1-C4 alkyl, and electron withdrawing groups; and each $Q^2$ is independently N or P.

In a further aspect, the Ar is aryl selected from

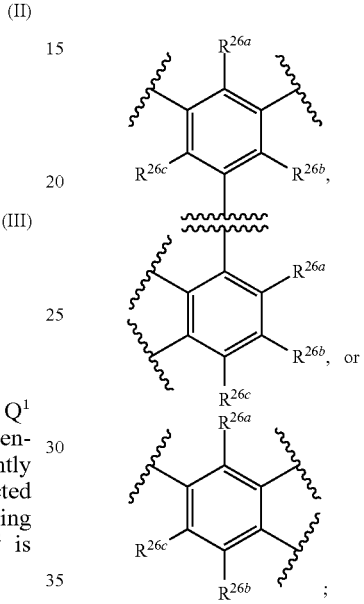

wherein each $R^{26a}$, $R^{26b}$, and $R^{26c}$ is independently selected from hydrogen, halogen, C1-C4 alkyl, and electron withdrawing groups.

In a further aspect, the oxygen scavenger compound can have the formula

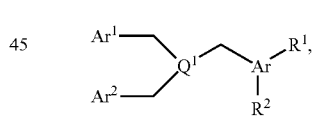

Ar is aryl; $Ar^1$ is aryl; $Ar^2$ is aryl; $R^1$ is hydrogen; $R^2$ is hydrogen; and the compound has the structure:

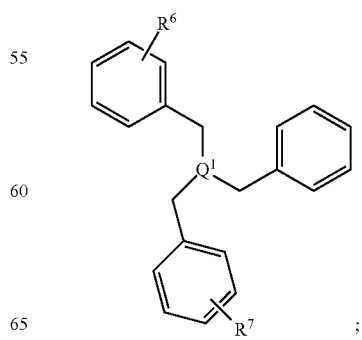

R⁶ represents five groups independently selected from hydrogen, halogen, C1-C4 alkyl, and electron withdrawing groups; provided that no less than two groups are hydrogen; and R⁷ represents five groups independently selected from hydrogen, halogen, C1-C4 alkyl, and electron withdrawing groups; provided that no less than two groups are hydrogen.

In a further aspect, the compound has the formula

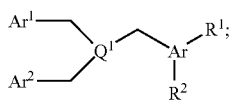
(I)

and Ar is aryl; Ar¹ is aryl; Ar² is aryl; R¹ is hydrogen; R² is

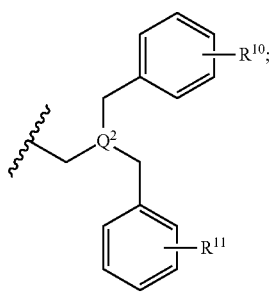

and the compound has the structure:

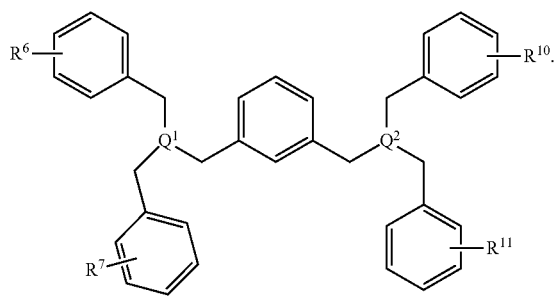

In a further aspect, the compound has the formula

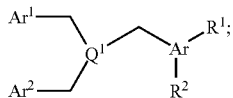
(I)

Ar is aryl; Ar¹ is aryl; Ar² is aryl; R¹ is hydrogen; R² is

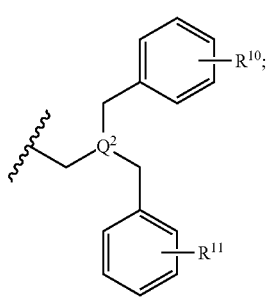

and the compound has the structure:

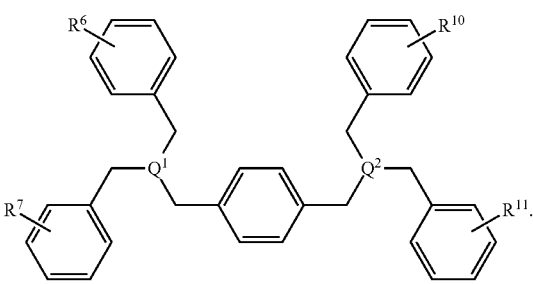

In a further aspect, the compound has the formula:

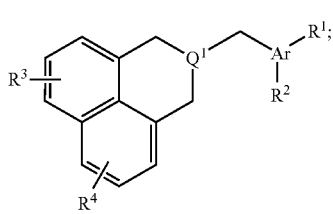
(II)

Ar is aryl; R¹ is hydrogen; R² is hydrogen; and the compound has the structure:

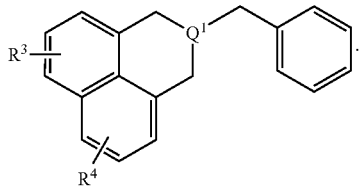

In a further aspect, the compound has the formula:

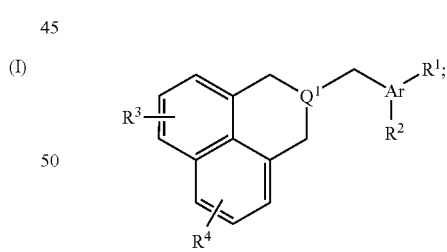
(II)

Ar is aryl; R¹ is hydrogen; R² is

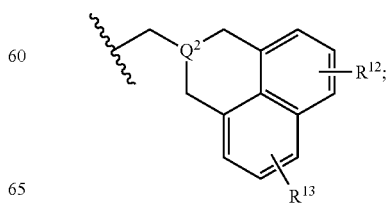

and the compound has the structure:

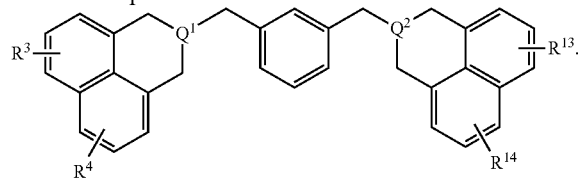

In a further aspect, the compound has the formula:

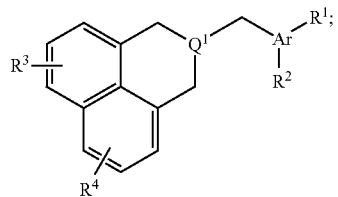
(II)

Ar is pyridine; R¹ is hydrogen; R² is hydrogen; and the compound has the structure:

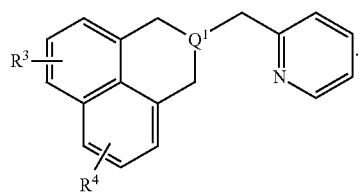

In a further aspect, the compound has the formula:

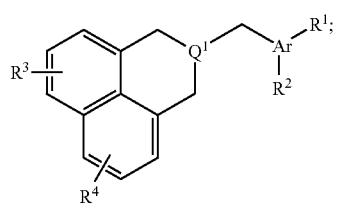
(II)

Ar is aryl; R¹ is hydrogen; R² is

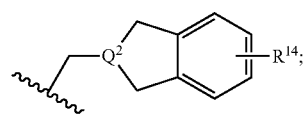

and the compound has the structure:

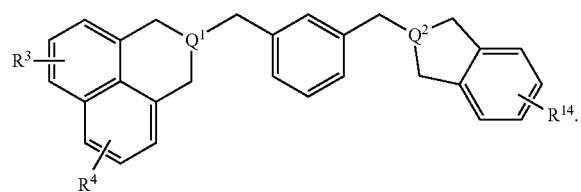

In a further aspect, the compound has the formula:

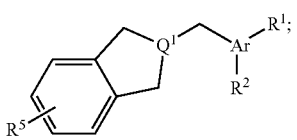
(III)

Ar is aryl; R¹ is hydrogen; R² is hydrogen; and the compound has the structure:

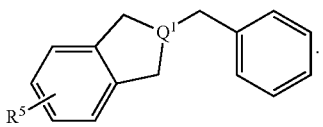

In a further aspect, the compound has the formula:

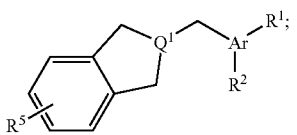
(III)

Ar is phenyl; R¹ is hydrogen; R² is

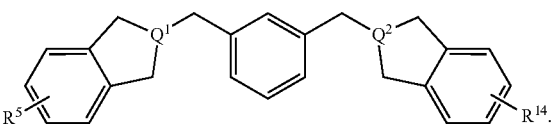

and the compound has the structure:

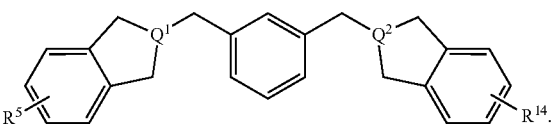

In a further aspect, Ar is monocyclic. In a still further aspect, Ar is para or meta substituted phenyl.

In a further aspect, the compound has the structure

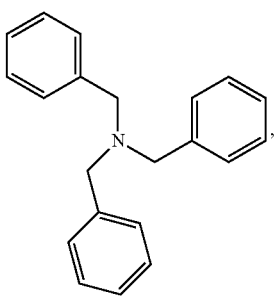

-continued

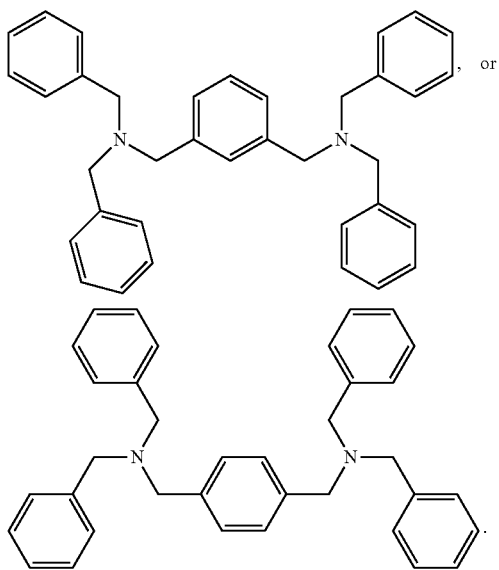, or

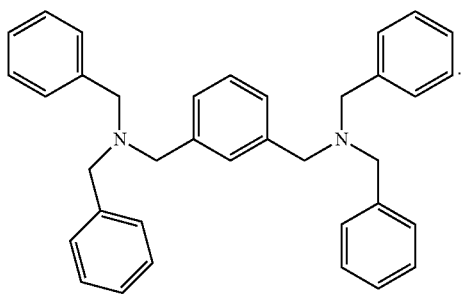 [SMILES: c1ccc(CN(Cc2ccccc2)Cc2cccc(CN(Cc3ccccc3)Cc3ccccc3)c2)cc1]

In some aspects, the compound has the structure:

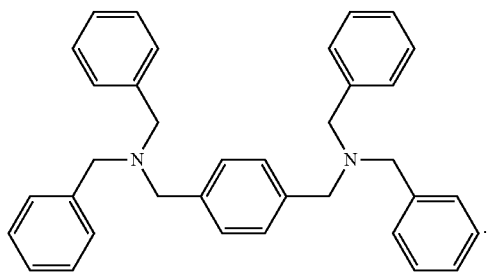 [SMILES: c1ccc(CN(Cc2ccccc2)Cc2ccc(CN(Cc3ccccc3)Cc3ccccc3)cc2)cc1]

In other aspects, the compound has the structure:

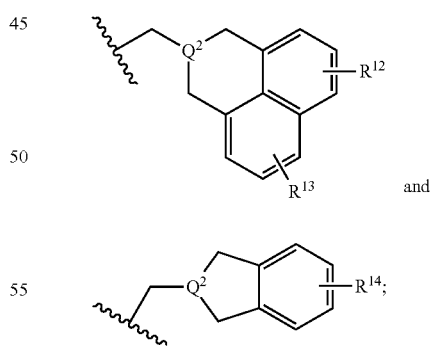

In a further aspect, the compound has the formula:

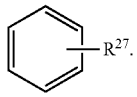
(IV)

In a still further aspect, $R^{27}$ represents six groups, each group independently selected from hydrogen,

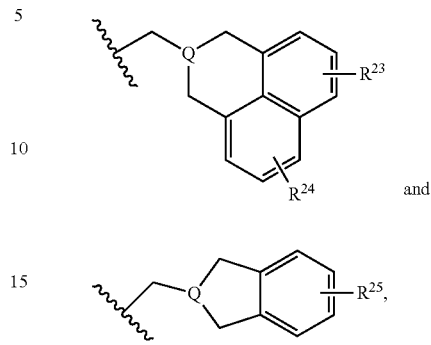 and provided that no more than four groups are hydrogen; and each Q is independently N or P. In a yet further aspect, $R^{23}$ represents three groups, each group independently selected from hydrogen, halogen, C1-C4 alkyl, and electron withdrawing groups; $R^{24}$ represents three groups, each group independently selected from hydrogen, halogen, C1-C4 alkyl, and electron withdrawing groups; and $R^{25}$ represents four groups, each group independently selected from hydrogen, halogen, C1-C4 alkyl, and electron withdrawing groups.

In a further aspect, the compound as the formula:

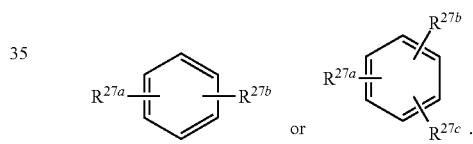

In a still further aspect, each $R^{27a}$, $R^{27b}$ and $R^{27c}$ are independently selected from

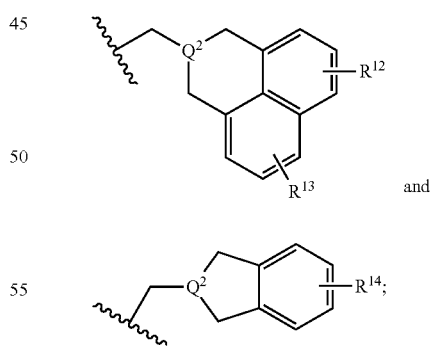

each Q is independently N or P; $R^{23}$ represents four groups, each group independently selected from hydrogen, halogen, C1-C4 alkyl, and electron withdrawing groups; $R^{24}$ represents three groups, each group independently selected from hydrogen, halogen, C1-C4 alkyl, and electron withdrawing groups; and $R^{25}$ represents four groups, each group independently selected from hydrogen, halogen, C1-C4 alkyl, and electron withdrawing groups.

In a still further aspect, each $R^{27a}$, $R^{27b}$ and $R^{27c}$ are independently selected from

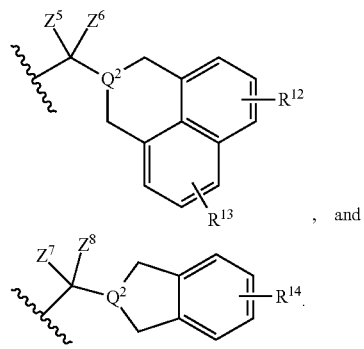

, and

In a still further aspect, each $R^{12}$ represents three groups independently selected from hydrogen, halogen, C1-C4 alkyl, and electron withdrawing groups; and $R^{13}$ represents three groups independently selected from hydrogen, halogen, C1-C4 alkyl, and electron withdrawing groups; and $R^{14}$ represents four groups independently selected from hydrogen, halogen, C1-C4 alkyl, and electron withdrawing groups; and each $Q^2$ is independently N or P; and each $Z^5$ and $Z^6$ are independently hydrogen, halogen, C1-C4 alkyl, electronic withdrawing group, electronic donating group; and each $Z^7$ and $Z^8$ are independently hydrogen, halogen, C1-C4 alkyl, electronic withdrawing group, or electronic donating group.

In a further aspect, the compound has the structure:

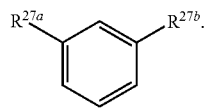

In a still further aspect, the compound has the structure:

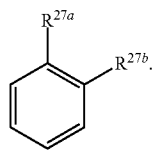

In a yet further aspect, the compound has the structure:

In an even further aspect, the compound has the structure:

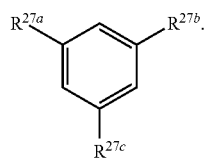

In a further aspect, the compound has the structure:

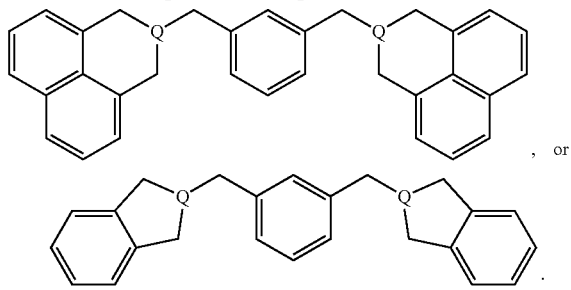

, or

In a still further aspect, the compound has the structure:

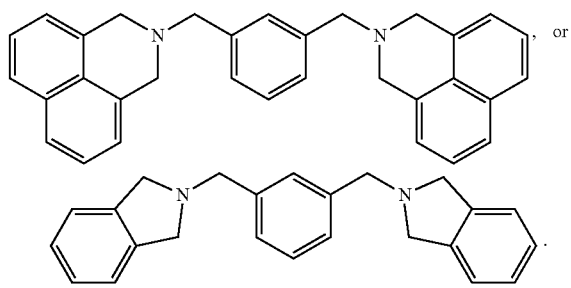

In a further aspect, the compound has the structure:

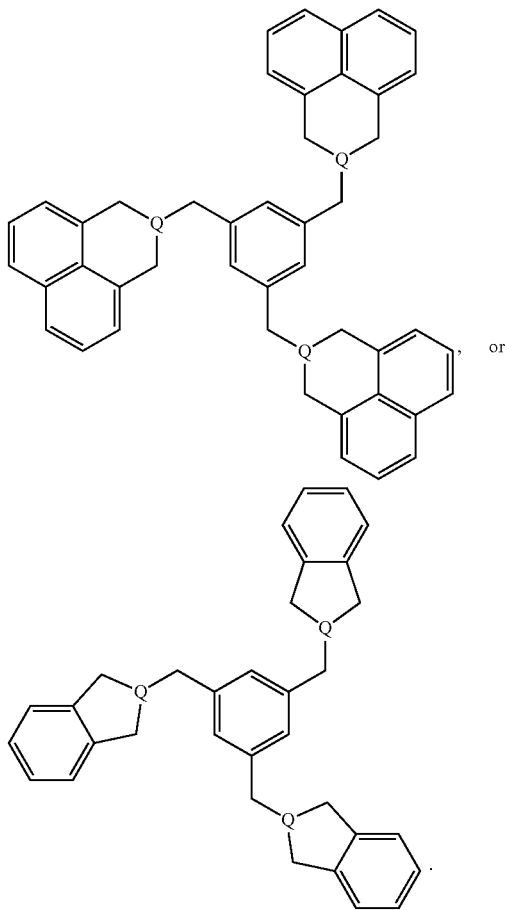

In a still further aspect, the compound has the structure:

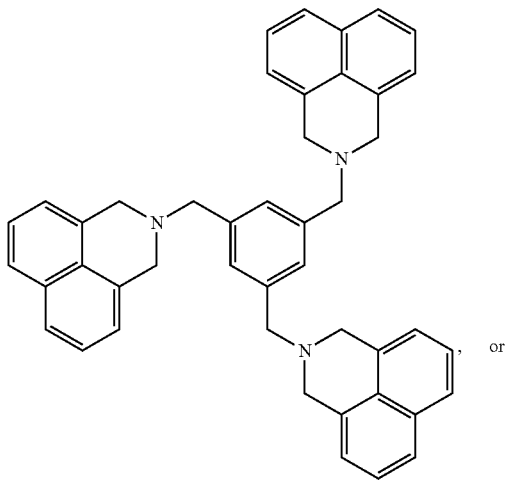, or

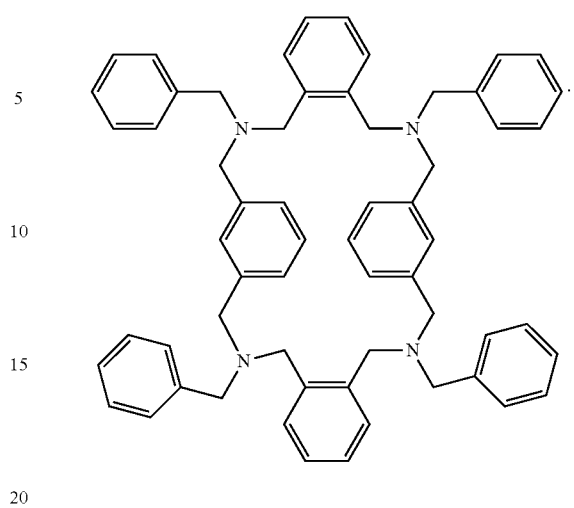

In a further aspect, the compound has the formula:

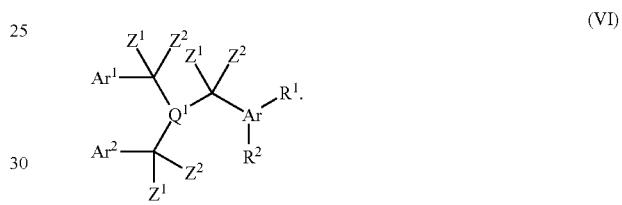 (VI)

In a still further aspect, Ar is aryl or heteroaryl; each $Q^1$ is independently N or P; each of $Ar^1$ and $Ar^2$ is independently aryl or heteroaryl; each $Ar^1$ and $Ar^2$ is independently substituted with 0, 1, 2, or 3 groups independently selected from halogen, C1-C4 alkyl, and electron withdrawing groups, and valence is satisfied; each $Z^1$ and $Z^2$ are independently hydrogen, halogen, C1-C4 alkyl, electronic withdrawing group, electronic donating group, or collectively =O; provided that at least one set of $Z^1$ and $Z^2$ are hydrogens; and each of $R^1$ and $R^2$ is independently selected from hydrogen,

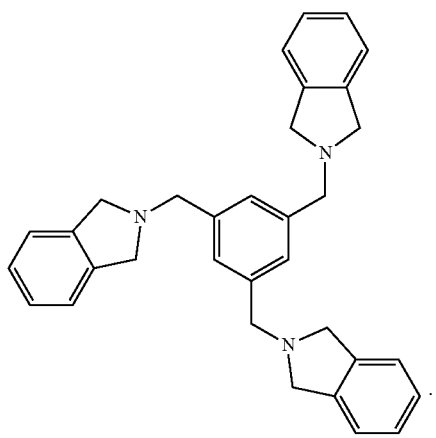

In a further aspect, the oxygen scavenger compound is polymeric or copolymeric. In a still further aspect, the compound has the formula

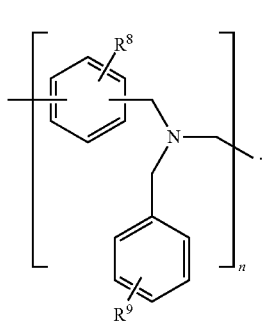 (V)

In a still further aspect, n is 3 or greater; $R^8$ and $R^9$ is independently selected from hydrogen, halogen, C1-C4 alkyl, and electron withdrawing groups.

In a further aspect, the compound is a cyclic polymeric compound. In a still further aspect, the compound has the structure:

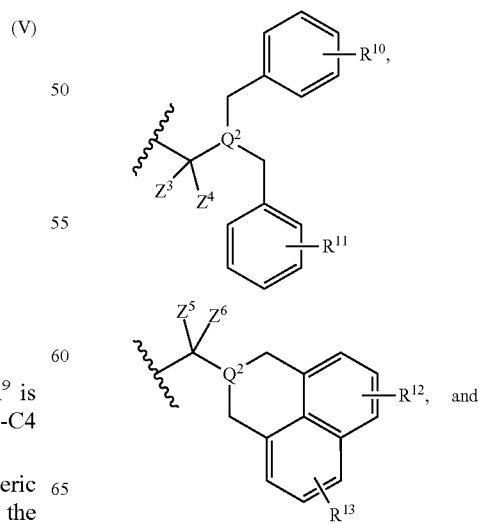

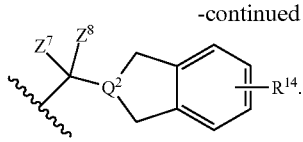

In a still further aspect, each $R^{10}$ represents five groups independently selected from hydrogen, halogen, C1-C4 alkyl, and electron withdrawing groups; $R^{11}$ represents five groups independently selected from hydrogen, halogen, C1-C4 alkyl, and electron withdrawing groups; and $R^{12}$ represents three groups independently selected from hydrogen, halogen, C1-C4 alkyl, and electron withdrawing groups; and $R^{13}$ represents three groups independently selected from hydrogen, halogen, C1-C4 alkyl, and electron withdrawing groups; and $R^{14}$ represents four groups independently selected from hydrogen, halogen, C1-C4 alkyl, and electron withdrawing groups; and each $Q^2$ is independently N or P; and each $Z^3$ and $Z^4$ are independently hydrogen, halogen, C1-C4 alkyl, electronic withdrawing group, electronic donating group, or collectively =O; each $Z^5$ and $Z^6$ are independently hydrogen, halogen, C1-C4 alkyl, electronic withdrawing group, electronic donating group, or collectively =O; and each $Z^7$ and $Z^8$ are independently hydrogen, halogen, C1-C4 alkyl, electronic withdrawing group, electronic donating group, or collectively =O.

In a further aspect, the compound has the formula:

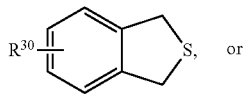

(VII)

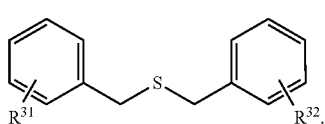

(IX)

In a still further aspect, each $R^{30}$ represents four groups, each group independently selected from hydrogen, halogen, C1-C4 alkyl, and electron withdrawing groups; $R^{31}$ represents three groups, each group independently selected from hydrogen, halogen, C1-C4 alkyl, and electron withdrawing groups; and $R^{32}$ represents four groups, each group independently selected from hydrogen, halogen, C1-C4 alkyl, and electron withdrawing groups.

In a further aspect, the compound has the structure

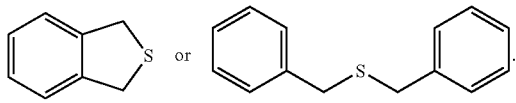 [SMILES: c1ccc2c(c1)CSC2 ; c1ccc(CSCc2ccccc2)cc1]

In a further aspect, the compound has the formula

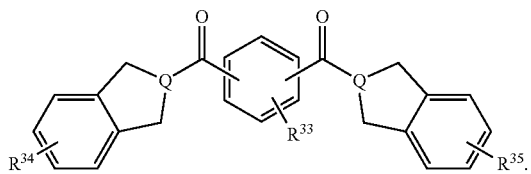

(IX)

In a further aspect, each Q is independently N or P; each $R^{33}$ represents four groups, each group independently selected from hydrogen, halogen, C1-C4 alkyl, electron donating groups, and

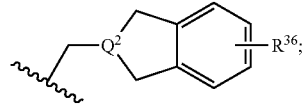

each $R^{36}$ represents four groups independently selected from hydrogen, halogen, C1-C4 alkyl, and electron donating groups; and each $Q^2$ is independently N or P; and $R^{34}$ represents four groups, each group independently selected from hydrogen, halogen, C1-C4 alkyl, and electron donating groups; and each $R^{35}$ represents four groups, each group independently selected from hydrogen, halogen, C1-C4 alkyl, and electron donating groups.

In a still further aspect, the compound has the structure

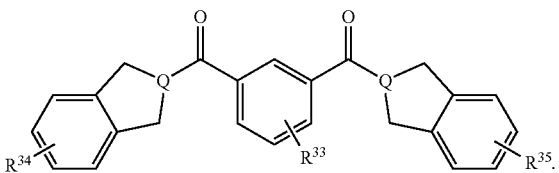

In a yet further aspect, the compound has the structure

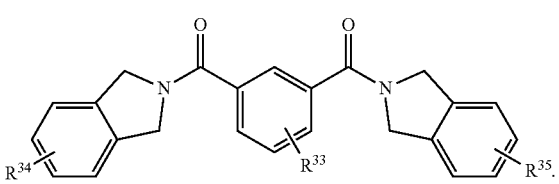

In an even further aspect, the compound has the structure

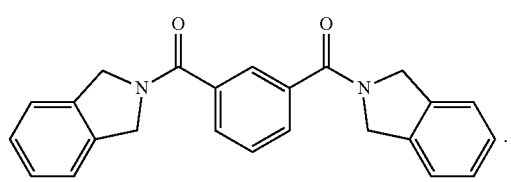 [SMILES: O=C(c1cccc(C(=O)N2Cc3ccccc3C2)c1)N1Cc2ccccc2C1]

In a further aspect, the alkyl group of the disclosed oxygen scavenging compound can be a branched or unbranched saturated hydrocarbon group of 1 to 24 carbon atoms, e.g. 1 to 18 carbons atoms, 1 to 14 carbon atoms, 1 to 12 carbon atoms, 1 to 10 carbon atoms, 1 to 8, 1 to 6 carbon atoms, or 1 to 4 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. The alkyl group can be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, halide, hydroxamate, hydroxy, ketone, nitro, silyl, sulfo-oxo, sulfonyl, sulfone, sulfoxide, or thiol, as described below. The alkyl group can be halogenated, which includes an alkyl group that is substituted with one or more halide, e.g., fluorine, chlorine, bromine, or iodine. The alkyl group can also be a lower alkyl group, which is an alkyl group containing from one to six (e.g., from one to four) carbon atoms.

In a further aspect, the aryl group of the disclosed oxygen scavenging compound can be any carbon-based aromatic group including but not limited to, benzene, naphthalene, phenyl, biphenyl, etc. The aryl group can also be heteroaryl, which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, halogenated alkyl, alkoxy, alkenyl, alkynyl, aryl, heteroaryl, aldehyde, amino, carboxylic acid, ester, halide, hydroxamate, hydroxy, ketone, nitro, silyl, sulfo-oxo, sulfonyl, sulfone, sulfoxide, or thiol as described herein. A biaryl group is a specific type of aryl group and is included in the definition of aryl. Biaryl refers to two aryl groups that are bound together via a fused ring structure, as in naphthalene, or are attached via one or more carbon-carbon bonds, as in biphenyl.

In a further aspect, suitable electron withdrawing groups and electron releasing or donating groups for use in the present invention are generally known in the art. Exemplary electron withdrawing groups include nitro, carboxylic acid, esters, for example loweralkyl esters, and cyano. Exemplary electron releasing groups include branched and straight chain alkyl groups, for example, methyl, ethyl, propyl, isopropyl, butyl, isobutyl, and tert-butyl. Other exemplary electron releasing groups include alkoxy, for example methoxy and ethoxy. Other exemplary electron releasing groups include thioalkyl. Still other exemplary electron releasing groups include amines, for example —$NH_2$, and NH(loweralkyl), and N(loweralkyl)$_2$.

The oxygen scavenging compound can, in certain aspects be complexed to a transition metal. For example, the oxygen scavenging compound can be complexed to the transition metal through one or more aryl groups, for example through pi-cloud complexation. The oxygen scavenging compound can also be polymerized via complexation to the transition metal.

2. Oxygen Scavenging Compositions

In various aspects, also disclosed herein are compositions comprising the oxygen scavengers. In one aspect, the disclosed compositions are oxygen scavenging compositions. Generally, the disclosed oxygen scavenging composition comprises a base polymer; an oxygen scavenger compound of Formula (I)-(IX) present in an amount of from about 0.10 to about 10 weight percent of the composition; and optionally, a transition metal in a positive oxidation state, the metal present in an amount of from about 10 ppm to about 400 ppm.

In a further aspect, the oxygen scavenging compositions comprise from about 0.10% to about 10% weight percent of the oxygen scavenger. In one aspect, the compositions comprise from about 0.5% to about 10% by weight of an oxygen scavenger. In still further aspect, the compositions comprise from about 1% to about 5% by weight of an oxygen scavenger. In a yet further aspect, the compositions comprise from about 0.1% to about 1% by weight of an oxygen scavenger. In a still further aspect, the compositions comprise from about 0.1% to about 5% by weight of an oxygen scavenger. In an even further aspect, the compositions comprise from about 3% to about 10% by weight of an oxygen scavenger. In a still further aspect, embodiment the compositions comprise from about 5% to about 10% by weight of an oxygen scavenger. In a yet further aspect, the compositions comprise from about 2% to about 7% by weight of an oxygen scavenger.

In various aspects, the disclosed compositions comprise a base polymer. In a further aspect, the base polymer can comprise one or more homopolymers or copolymers as described herein. In one aspect, the compositions can comprise from about 80% to about 99.98% by weight of a base polymer. In a further aspect, the composition comprises from about 80% to about 99% by weight of a base polymer. In a still further aspect, the composition comprises from about 85% to about 99% by weight of a base polymer. In a yet further aspect, the composition comprises from about 90% to about 99.98% by weight of a base polymer. In an even further embodiment the composition comprises from about 95% to about 99% by weight of a base polymer. In a still further aspect, the composition comprises from about 95% to about 99.98% by weight of a base polymer. In a yet further aspect, the composition comprises from about 97% to about 99% by weight of a base polymer.

In a further aspect, a variety of different polymers can be used as the base polymer. The disclosed compositions enable oxygen scavenging, and thus the base polymer generally includes those polymers that can be subject to oxidation. For example, polymers that exhibit at least some oxygen permeability are useful with the disclosed compositions, at least inasmuch as the disclosed compositions can reduce the oxidative damage to the polymer.

In a further aspect, the base polymer can be a polymer commonly used in packaging materials including polyethylene, such as low density polyethylene, very low density polyethylene, ultra-low density polyethylene, high density polyethylene, and linear low density polyethylene; polyesters such as (PET), (PEN) and their copolymers such as PET/IP; polyvinyl chloride (PVC); polyvinylidene chloride (PVDC); and ethylene copolymers such as ethylene/vinyl acetate copolymer, ethylene/alkyl(meth)acrylate copolymers, ethylene/(meth)acrylic acid copolymers, and ionomers. Blends of different base polymers also can be used.

In a further aspect, the base polymer can include one or more polymers approved by the U.S. Food and Drug Administration (FDA). Non-limiting examples include polyethylene terephthalate, polypropylene, and polyethylene.

In a further aspect, the base polymer comprises a polyester polymer or copolymer. Preferred polyesters include polymers of phthalic acids, such as polyethylene terephthalate (PET), or a copolymer thereof. PET, for example, can be made from terephthalic acid and ethylene glycol. PET can also be made using dimethyl terephthalate and ethylene glycol. Preferred copolymers of phthalic acids include copolymers of a phthalic acid and one or more hydroxylated organic compounds. Examples of suitable hydroxylated organic compounds include 1,4-cyclohexandedimethanol, 1,2-propanediol, 1,4-butanediol, 2,2-dimethyl-1,3-propanediol, 2-methyl-1,3-propanediol (2MPDO), 1,6-hexanediol, 1,2-cyclohexanediol, 1,4-cyclohexanediol, 1,2-cyclohexanedimethanol, 1,3-cyclohexanedimethanol, and diols containing one or more oxygen atoms in the chain, e.g., diethylene glycol, triethylene glycol, dipropylene glycol, tripropylene glycol, or mixtures of these, and the like.

In a further aspect, the base polymer includes a polyethylene terephthalate homopolymer and copolymer modified with one or more polycarboxylic acid modifiers in a cumulative amount of less than about 15 mole %, or about 10 mole % or less, or about 8 mole % or less, or one or more hydroxyl compound modifiers in an amount of less than about 60 mol %, or less than about 50 mole %, or less than about 40 mole %, or less than about 15 mole %, or about 10 mole % or less, or about 8 mole % or less and polyethylene naphthalate homopolymers and copolymers modified with a cumulative amount of less than about 15 mole %, or about 10 mole % or less, or about 8 mole % or less, of one or more polycarboxylic acid modifiers or modified with less than about 60 mol %, or less than about 50 mole %, or less than about 40 mole %, or less than about 15 mole %, or about 10 mole % or less, or about 8 mole % or less of one or more hydroxyl compound modifiers, and blends thereof. In some aspects, the base polymer comprises at least 90 mole %, 92 mole %, or 94 mole % ethylene terephthalate repeat units based on the moles of all repeat units in the polyester polymers.

Polyesters such as PET can be prepared by polymerization procedures known in the art sufficient to effect esterification and polycondensation. Polyester melt phase manufacturing processes include direct condensation of a dicarboxylic acid with a diol, optionally in the presence of one or more esterification catalysts, in the esterification zone, followed by polycondensation in the prepolymer and finishing zones in the presence of a polycondensation catalyst; or ester exchange usually in the presence of a transesterification catalyst in the ester exchange zone, followed by prepolymerization and polymerization in the presence of a polycondensation catalyst.

As briefly discussed above, the disclosed compositions and articles can comprise a transition metal in a positive oxidation state. The transition metal enhances the oxygen scavenging properties of the oxygen scavenger compound. Amounts of transition metal in the composition can be greater than zero and can be up to 5000 ppm. Generally, the transition metal will be present in an amount of from about 10 ppm to about 400 ppm. In one aspect, about 200 ppm of the transition metal is present. In a further aspect, about 250 ppm of the transition metal is present. In wall applications (as opposed to master batch applications where more transition metal is used), it can be preferred to keep the level of metal below 300, more preferably 250 ppm. In a further aspect, the transition metal is present from 30 to 150 ppm. In a further aspect, about 50 ppm of the transition metal is present. In a further aspect, about 100 ppm of the transition metal is present. In a further aspect, about 150 ppm of the transition metal is present.

In a further aspect, the transition metal can be a transition metal from the first, second, or third transition series of the Periodic Table. The metal can be Rh, Ru, or one of the elements in the series of Sc to Zn (e.g., Sc, Ti, V, Cr, Mn, Fe, Co, Ni, Cu, and Zn). In one aspect, the transition metal is cobalt. Cobalt can be used in +2 or +3 oxidation states. In some aspects, it is preferred to use cobalt in the +2 oxidation state. In a further aspect, the transition metal is rhodium. For example, rhodium in the +2 oxidation state can be used. The transition metal can also be a positive oxidation form of zinc.

In a further aspect, the transition metal can be present as a salt. The cation of the salt can be the transition metal in a positive oxidation state. A variety of anions can stabilize the positively charged transition metal. Suitable anions for the salts include, but are not limited to, chloride, acetate, oleate, stearate, palmitate, 2-ethylhexanoate, carboxylates, such as neodecanoates, octanoates, acetates, lactates, naphthalates, malates, stearates, acetylacetonates, linoleates, oleates, palmitates, 2-ethylhexanoates, or ethylene glycolates; or as their oxides, borates, carbonates, dioxides, hydroxides, nitrates, phosphates, sulfates, or silicates, among others. Representative transition metal salts include cobalt (II) 2-ethylhexanoate, cobalt oleate, and cobalt (II) neodecanoate. The transition metal salt also can be an ionomer, in which case a polymeric counter ion can be present.

In a further aspect, the composition can comprise a colorant in a visually effective amount. A visually effective amount refers to an amount of colorant that results in the composition or an article made therefrom appear colored to the naked eye. A composition comprising a visually effective amount of colorant can refer to a composition having at least 0.01% by weight colorant. In a further aspect, the composition can comprise at least 0.25% by weight colorant. In a still further aspect, the composition can comprise at least 0.5% by weight colorant. The compositions can also comprise up to or even exceed about 3% by weight colorant.

A visually effective amount can be determined, for example, by performing a spectrophotometric scan of the composition or article using a wavelength range from 400 to 700 nm (visible region). Specific colors can be characterized according to their spectral pattern. Every color also has its own characteristic L (lightness gradation), a (red to green) and b (yellow to blue) numbers, which can be used to characterize the compositions and articles.

The colorant can be a variety of pigments and dyes, many of which are commercially available. Examples of colorants include without limitation COLORMATRIX Dark Amber, product code: 189-10034-6, COLORMATRIX Dead Leaf Green, product codes: 284-2801-3 and 84-2801-1, AMERICHEM amber, product code: 59108-CD1, Champaigne green, and COLORMATRIX amber, product code: 189-10100-1.

In various aspects, the composition can include other components such as fillers, crystallization aids, impact modifiers, surface lubricants, denesting agents, stabilizers, ultraviolet light absorbing agents, metal deactivators, nucleating agents such as polyethylene and polypropylene, phosphate stabilizers and dyestuffs. Typically, the total quantity of such components will be less than about 10% by weight of the composition. In some embodiments, the amount of these optional components is less than about 5% by weight of the composition.

In a further aspect, the composition can comprise a reheat additive. Reheat additives are commonly used in the manufacture of polyester polymer compositions used to make stretch blow molded bottles because the preforms made from the composition must be reheated prior to entering the mold for stretch blowing into a bottle. Any conventional reheat additive can be used, such as various forms of black particles, e.g., carbon black, activated carbon, black iron oxide, glassy carbon, silicon carbide, gray particles such as antimony, and other reheat additives such as silicas, red iron oxide, and the like.

In a further aspect, the composition can also comprise an impact modifier. Examples of typical impact modifiers useful in the composition include ethylene/acrylate/glycidyl terpolymers and ethylene/acrylate copolymers in which the acrylate is a methyl or ethyl acrylate or methyl or ethyl methacrylate or the corresponding butyl acrylates, styrene based block copolymers, and various acrylic core/shell type impact modifiers. The impact modifiers can be used in conventional amounts from about 0.1 to about 25 weight percent of the overall composition and, in some aspects, in amounts from about 0.1 to about 10 weight percent of the composition.

In many applications, not only are the packaging contents sensitive to the ingress of oxygen, but the contents may also be affected by UV light. Fruit juices and pharmaceuticals are two examples of such contents. Accordingly, in some aspects, it is desirable to incorporate into the composition a UV absorbing compound in an amount effective to protect the packaged contents.

In a further aspect, the disclosed composition or an article made therefrom can have an Oxygen Transmission Rate (OTR) of less than about 0.1 (units of cc/pkg/day or 1-5 cc-mm/m²-day-atm) under standard conditions. In a further aspect, the OTR can be less than 0.03, less than 0.01, less than 0.005, or less than 0.001. The OTR is a measure of how well the oxygen scavenger compound functions at scavenging oxygen that permeates the composition or article.

When OTR is expressed for a given composition or article, the units "cc/package/day" ("cc/pkg/day") are typically employed. The term package refers to a barrier between an atmosphere of relatively lower oxygen content and an atmosphere of relatively higher oxygen content. Typical barriers (e.g., packages) include bottles, thermoformed containers, and films (e.g., shrink wrap).

Oxygen Transmission Rate (oxygen permeation) can be measured, for example, as described in U.S. Pat. No. 5,021,515. A material of area A can be exposed to a partial pressure p of oxygen on the one side and to an essentially zero partial pressure of oxygen on the other side. The quantity of oxygen emerging on the latter side is measured and expressed as a volume rate dV/dt, the volume being converted to some standard condition of temperature and pressure. After a certain time of exposure (usually a period of a few days) dV/dt is generally found to stabilize, and a $P_W$ value can be calculated from equation below:

$$dV/dt = P_W A_p \quad (1)$$

$P_W$ refers to the permeance of the wall. (Analogy with magnetic permeance and electrical conductance would suggest that $P_W$ should be described as "permeance per unit area", but we are following the nomenclature in Encyclopedia of Polymer Science and Technology, Vol. 2, Wiley Interscience, 1985, page 178.) The standard conditions for expressing dV/dt are 0° C. and 1 atm (1 atm=101 325 Nm$^{-2}$). If the thickness of the area of wall is substantially constant over the area A with value T and the wall is uniform through the thickness (i.e., the wall is not a laminated or coated one) then the permeability of the material in the direction normal to the wall is calculated from the equation below.

$$dV/dt = P_M A p/T \quad (2)$$

For non-scavenging materials, $P_W$ and $P_M$ are to a reasonable approximation independent of t and p, and $P_M$ of T although they are often appreciably dependent on other conditions of the measurement such as the humidity of the atmosphere on the oxygen-rich side and the temperature of the measurement.

For oxygen-scavenging walls, $P_W$ and $P_M$ are functions of t because the concentrations and activity of scavenger vary with time (particularly as the scavenger is consumed). This typically does not prevent measurement of $P_W$ and $P_M$ reasonably accurately as a function of time, because the changes in dV/dt are relatively gradual once the normal initial equilibration period of a few days is over. After a few days' exposure to the measurement conditions, however, a non-scavenging material typically achieves a steady state in which dV/dt is equal to the rate of oxygen ingress to the wall, while a scavenging material achieves an (almost) steady state in which dV/dt is considerably less than the rate of oxygen ingress to the material. This being the case, it is likely that $P_W$ calculated from (1) is a function of p as well as of t and that $P_M$ in (2) is a function of p and T as well as of t. $P_W$ and $P_M$ for scavenging materials are, strictly speaking, not true permeances and permeabilities at all (since permeation and scavenging are occurring simultaneously) but, rather, apparent ones.

Values of $P_W$ and $P_M$ (except where stated otherwise) are to be understood to refer to conditions in which p=0.21 atm, the relative humidity on the oxygen-rich side of the wall is 50%, the temperature is 23° C. and (in the case of $P_M$ values) the thickness of the material of about 0.45 mm. Conditions close to the first three of these, at least, are conventional in the packaging industry.

For example, OTR can be measured for bottles, for example, by controlling the atmosphere on both sides of a sample of bottles and measuring the rate of oxygen permeation over time. Typically, the bottles are mounted on a plate such that there are two ports for gas inlet and outlet. The interior of the bottles is separated from the exterior by an air tight seal. After sealing, the interior of the bottle is flushed with $N_2$ gas (or $N_2+H_2$ mixture) to remove any oxygen present before mounting on plate. The bottle is then placed in a controlled environmental chamber (maintained at 23° C. and 50% RH) such that the exterior of the bottle is at standard atmosphere with ~21% oxygen. The interior of the bottle is continuously flushed with $N_2$ (or $N_2+H_2$) at a known gas flow rate. The outlet of the flushed gases contains oxygen permeating through the bottle wall. This flushed gas from the bottle interior is passed over a sensor that is calibrated to measure oxygen content of the flushed gas. Such measurements of oxygen content are made continuously over time until a steady state is reached. This steady state value is typically reported as Oxygen Transmission Rate (OTR) for that bottle in the units of cc/package/day. A preferred OTR for PET bottles is less than 0.1 cc/package/day; more preferred is less than 0.01 cc/package/day; most preferred for PET bottles is less than 0.001 cc/package/day over the shelf life of the packaged product.

In one aspect, a disclosed composition has an OTR of less than that of an otherwise identical composition in the absence of the oxygen scavenger compound and the transition metal. In a further aspect, a disclosed composition has an OTR of less than about 75%, less than about 50%, less than about 25%, less than about 20%, less than about 10%, less than about 5%, or less than about 1% of an otherwise identical composition in the absence of the oxygen scavenger compound and the transition metal.

In one aspect, the invention provides oxygen scavenging compositions that react with oxygen in the presence of transition metals and salts thereof, comprising, an effective amount of a disclosed oxygen scavenger compound.

In a further aspect, the invention provides oxygen scavenging compositions that react with oxygen in the presence of transition metals and salts thereof, comprising, an effective amount of a compound of Formula (I)-(IX).

In a further aspect, the invention provides an oxygen scavenging system comprising: (a) an oxygen scavenging composition, comprising a compound of Formula (I)-(IX); (b) an effective amount of a transition metal catalyst; and (c) a functional barrier permeable to oxygen.

In a further aspect, the invention also relates to organic material normally susceptible to gradual degradation in the presence of oxygen during use over an extended period containing an antioxidant effective, or oxygen scavenging effective amount of a disclosed oxygen scavenger compound.

In a further aspect, the invention also relates to organic material normally susceptible to gradual degradation in the presence of oxygen during use over an extended period containing an antioxidant effective, or oxygen scavenging effective amount of a compound of of Formula (I)-(IX).

C. Methods

In various aspects, the invention relates to methods for making the disclosed compounds. In a further aspect, oxygen scavengers of the present invention can be synthesized by reacting about four moles of benzyl chloride with about 1 mole of meta-xylylenediamine (MXDA) under conditions effective to produce the desired product, as depicted below:

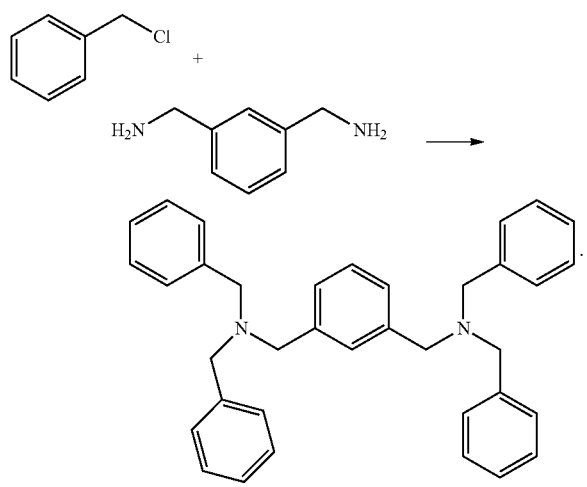

In a further aspect, the disclosed oxygen scavengers can be produced via reductions from related amides, which can be synthesized via condensation reactions. In a still further aspect, about 2 moles of phthalic anhydride is reacted with about 1 mole of meta-xylylenediamine (MXDA) under conditions effective to produce a diimide product, which can then be reduced under conditions effective to produce the desired product, as depicted below:

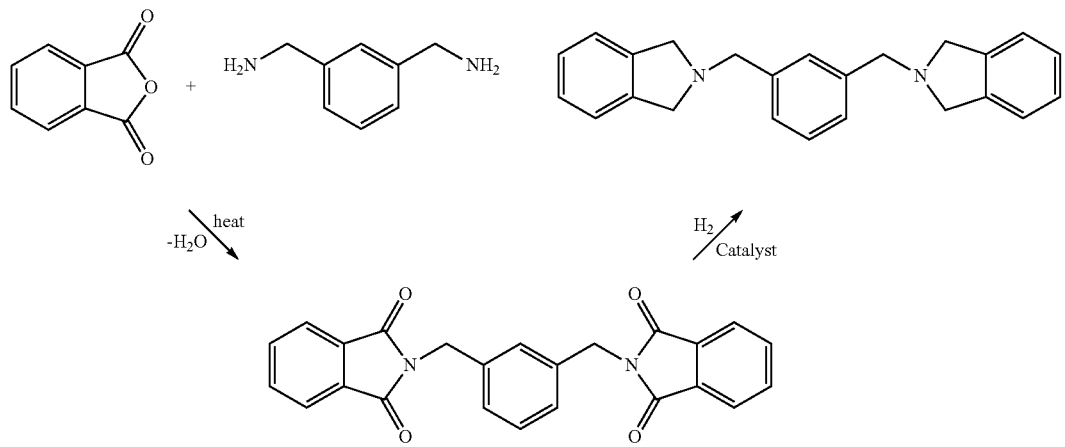

Further embodiments of the present invention can be prepared using methods and modifications known generally in the art.

In a further aspect, the invention also relates to methods for making the disclosed compositions. Various methods exist for making the disclosed compositions. In one aspect, the composition can be made by mixing the base polymer with the oxygen scavenger compound and optionally the transition metal. In some aspects, some or part of the transition metal may already be present in the base polymer prior to mixing, for example if the transition metal is used as a catalyst for making the base polymer. In some aspects, the base polymer, the oxidizable organic component or oxygen scavenger and the transition metal are mixed by tumbling in a hopper. Other optional ingredients can be added during this mixing process or added to the mixture after the aforementioned mixing or to an individual component prior to the aforementioned mixing step.

When melt processing is desired for the composition, the composition can also be made by adding each ingredient separately and mixing the ingredients just prior to melt processing the composition to form an article. In some embodiments, the mixing can be just prior to the melt process zone. In other embodiments, one or more ingredients can be premixed in a separate step prior to bringing all of the ingredients together.

In some aspects, the transition metal can be added neat or in a carrier (such as a liquid or wax) to an extruder or other device for making the article, or the metal can be present in a concentrate or carrier with the oxygen scavenger compound, in a concentrate or carrier with the base polymer, or in a concentrate or carrier with a base polymer/oxygen scavenger compound blend. It is desirable that the addition of the transition metal does not substantially increase the intrinsic viscosity of the melt in the melt processing zone. Thus, transition metal or metals can be added in two or more stages, such as once during the melt phase for the production of the base polymer and again once more to the melting zone for making the article.

The melt blend of base polymer, oxygen scavenger compound, and transition metal catalyst can also be prepared by adding the components at the throat of an injection molding machine that: (i) produces a preform that can be stretch blow molded into the shape of the container, (ii) produces a film that can be oriented into a packaging film, (iii) produces a sheet that can be thermoformed into a food tray, or (iv) produces an injection molded container. The mixing section of the extruder should be of a design to produce a homogeneous blend. Such process steps work well for forming carbonated soft drink, water or beer bottles, packaging films and thermoformed trays. The present invention can be employed in any of the conventional known processes for producing a polymeric container, film, tray, or other article that would benefit from oxygen scavenging.

According to further aspects of the disclosure, the invention provides methods for packaging an oxygen sensitive material, comprising: (a) preparing a package having a wall comprising at least one layer, at least one of the layers comprising a composition, the composition, comprising: (i) a base polymer; (ii) at least one compound of Formula (I)-(IX); and (iii) at least one transition metal in a positive oxidation state, the metal being present in the composition in an amount of 10 to 400 ppm; wherein the compound is present in an amount of about 0.10 to 10 weight percent of the composition; (b) introducing the oxygen sensitive material into the package; and (c) closing the package.

D. Articles

In further aspects, the present invention also relates to articles comprising the disclosed compounds and compositions. Various articles can be prepared from the disclosed compositions. Thus, the articles prepared from the compositions will also have the composition present in the article. Suitable articles include vessels and films, such as flexible sheet films, flexible bags, pouches, semi-rigid and rigid containers such as bottles (e.g. PET bottles) or metal cans, or combinations thereof. Typical flexible films and bags include those used to package various food items and can be made up of one or a multiplicity of layers to form the overall film or bag-like packaging material. The composition of the present invention can be used in one, some or all of the layers of such packaging material.

Specific articles include preforms, containers and films for packaging of food, beverages, cosmetics, pharmaceuticals, and personal care products where a high oxygen barrier is needed. Examples of beverage containers are bottles for holding water and carbonated soft drinks, and the invention is particularly useful in bottle applications containing juices, sport drinks, beer or any other beverage where oxygen detrimentally affects the flavor, fragrance, performance (e.g., vitamin degradation), or color of the drink. The compositions are also particularly useful as a sheet for thermoforming into rigid packages and films for flexible structures. Rigid packages include food trays and lids. Examples of food tray applications include dual ovenable food trays, or cold storage food trays, both in the base container and in the lidding (whether a thermoformed lid or a film), where the freshness of the food contents can decay with the ingress of oxygen. The compositions can also be used in the manufacture of cosmetic containers and containers for pharmaceuticals or medical devices.

Other suitable articles include rigid or semi-rigid articles including plastic, such as those utilized for juices, soft drinks, as well as thermoformed trays or cup normally having thickness in the range of from 100 to 1000 micrometers. The walls of such articles can comprise single or multiple layers of materials. The article can also take the form of a bottle or can, or a crown, cap, crown or cap liner, plastisol or gasket. The composition of the present invention can be used as an integral layer or portion of, or as an external or internal coating or liner of, the formed semi-rigid or rigid packaging article. As a liner, the composition can be extruded as a film along with the rigid article itself, e.g., by coextrusion, extrusion coating, or an extrusion lamination process, so as to form the liner in situ during article production; or alternatively can be adhered by heat and/or pressure, by adhesive, or by any other suitable method.

In a further aspect, the disclosed compositions can be used for forming a layer of a wall which primarily provides oxygen-scavenging (another layer including polymer providing gas barrier without significant scavenging), or as a head-space scavenger (completely enclosed, together with the package contents, by a package wall). When the compositions are used in a wall or as a layer of a wall, the permeability of the composition for oxygen is advantageously not more than about 3.0, or about 1.7, or about 0.7, or about 0.2, or about 0.03 $cm^3$-mm/($m^2$-atm-day). In some aspects, the permeability of the composition is not more than about three-quarters of that in the absence of the oxygen scavenger compound. In other aspects, the permeability is not more than about one half, one-tenth in certain embodiments, one twenty-fifth in other embodiments, and not more than one-hundredth of that in the absence of the oxygen scavenger compound.

Although it can be preferable from the standpoint of packaging convenience and/or scavenging effectiveness to employ the present invention as an integral or discrete part of the packaging wall, the invention can also be used as a non-integral component of a packaging article such as, for example, a bottle cap liner, adhesive or non-adhesive sheet insert, sealant, sachet, fibrous mat insert or the like.

Besides articles applicable for packaging food and beverage, articles for packaging other oxygen-sensitive products can also benefit from the present invention. Such products would include pharmaceuticals, oxygen sensitive medical products, corrodible metals or products, electronic devices and the like.

In a further aspect, the composition can be used as a master batch for blending with a polymer or a polymer containing component. In such compositions, the concentration of the oxygen scavenger compound and the transition metal will be high enough to allow for the final blended product to have suitable amounts of these components. The master batch can also contain an amount of the base polymer with which the master batch is blended.

Oxygen permeability of an article can be maintained for a longer period of time by storing the article in a sealed container or under an inert atmosphere such as nitrogen prior to use with oxygen sensitive materials.

In one aspect, the invention provides containers comprising a film forming polymer, having at least one wall comprising an effective amount of an oxygen scavenging composition comprising a disclosed oxygen scavenger compound.

In a further aspect, the invention provides containers comprising a film forming polymer, having at least one wall comprising an effective amount of an oxygen scavenging composition comprising a compound Formula (I)-(IX).

In a further aspect, the invention provides package walls comprising at least one layer, the layer comprising a composition, the composition comprising: (a) a base polymer; (b) at least one compound of Formula (I)-(IX); and (c) at least one transition metal in a positive oxidation state, the metal being present in the composition in an amount of 10 to 400 ppm; wherein the compound is present in an amount of about 0.10 to 10 weight percent of the composition.

In a further aspect, the invention provides package walls, comprising a composition, the composition comprising: (a) one or more outer layers; and (b) one or more inner layers; wherein at least one of the inner or at least one of the outer layers comprises a composition comprising: (1) a base polymer; (2) at least one compound of formula (I)-(IX); and (3) at least one transition metal in a positive oxidation state, the metal being present in the composition in an amount of 10 to 400 ppm; wherein the compound is present in an amount of about 0.10 to 10 weight percent of the composition. In some aspects, the first layer is disposed radially outward from the second layer.

The articles can be made by various methods known in the art. Generally, the articles are prepared by melt processing methods (i.e., a melt of the composition). Such processes generally include injection molding, stretch blow molding, extrusion, thermoforming, extrusion blow molding, and (specifically for multilayer structures) co-extrusion and lamination using adhesive tie layers. Orientation, e.g., by stretch blow molding, of the polymer can be used with phthalate polyesters because of the known mechanical advantages that result.

The melt processing zone for making the article can be operated under customary conditions effective for making the intended articles, such as preforms, bottles, trays, and other articles mentioned above. In one aspect, such conditions are effective to process the melt without substantially increasing the intrinsic viscosity of the melt and which are ineffective at promoting transesterification reactions. In some preferred aspects, suitable operating conditions effective to establish a physical blend of the base polymer, oxidizable organic component, and transition metal are temperatures in the melt processing zone within a range of about 250° C. to about 300° C. at a total cycle time of less than about 6 minutes, and typically without the application of vacuum and under a positive pressure ranging from about 0 psig (pound-force per square inch gauge) to about 900 psig. In some embodiments, the residence time of the melt on the screw can range from about 1 to about 4 minutes.

In one aspect, the invention provides methods for producing a packaging material having a wall with oxygen barrier properties comprising: (a) combining a base polymer with at least one compound of formula (I)-(IX) to form a composition, the composition having at least one transition metal in a positive oxidation state, the metal being present in the composition in an amount of 10 to 400 ppm; and wherein the compound is present in an amount of about 0.10 to 10 weight present of the composition; (b) forming the product of step (a) into a wall; and (c) forming a container which comprises the wall.

In a further aspect, the invention provides methods for making an article, comprising: (a) forming a melt by combining in a melt processing zone: (i) a base polymer; (ii) at least one compound of formula (I)-(IX), and (iii) at least one transition metal in a positive oxidation state, the metal being present in the composition in an amount of 10 to 400 ppm; wherein the compound is present in an amount of about 0.10 to 10 weight present of the composition; (b) forming an article from the melt.

E. Experimental

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: Synthesis of benzene-1,3-diylbis(N,N-dibenzylmethanamine):

In a first synthetic scheme, about 230 mL of benzyl chloride and 65 mL of meta-xylylenediamine (MXDA) was dissolved in tetrahydrofuran (THF) at room temperature. 4.4 L of 0.5M sodium hydroxide aqueous solution was then added to the mixture, and the mixture was subsequently stirred vigorously at room temperature overnight to produce the product, benzene-1,3-diylbis(N,N-dibenzylmethanamine), or dTBA.

Following completion of the reaction, the product remains almost exclusively in the THF layer, allowing for separation and purification using standard methods. The reactants and intermediates can also be recycled from the water layer and combined into a subsequent reaction batch, without a loss in product yield.

In an alternative embodiment using a slightly higher temperature of 80° C., the reaction can proceed quicker when in an aqueous $NaHCO_3$ medium with sodium dodecyl sulfate as a surfactant to assist in solubilizing the reactants.

The reaction scheme is depicted below:

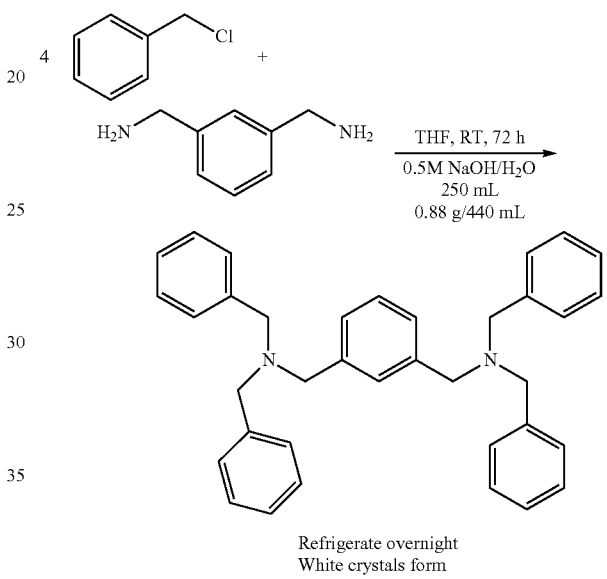

Refrigerate overnight
White crystals form

2. Example 2: Oxygen Scavenging Performance of TBA in Polyethylene Terephthalate:

Oxygen scavenging performance of the oxygen scavenging compositions of the present invention in different resins were evaluated using Oxysense™. Oxygen Transmission Rate can be calculated from OxySense data. OxySense measurements were carried out in a sealed OxyVial with a Ruthenium dye-based sensitizer attached to the inside wall of the vial. Upon illumination at a specific wavelength, the sensitizer gives off luminescence the intensity of which is correlated with the concentration of the oxygen in the vial. As a result, a trace of oxygen concentration change as a function of time can be plotted. The tests can be performed at higher temperatures to speed up the tests.

Figure 2:
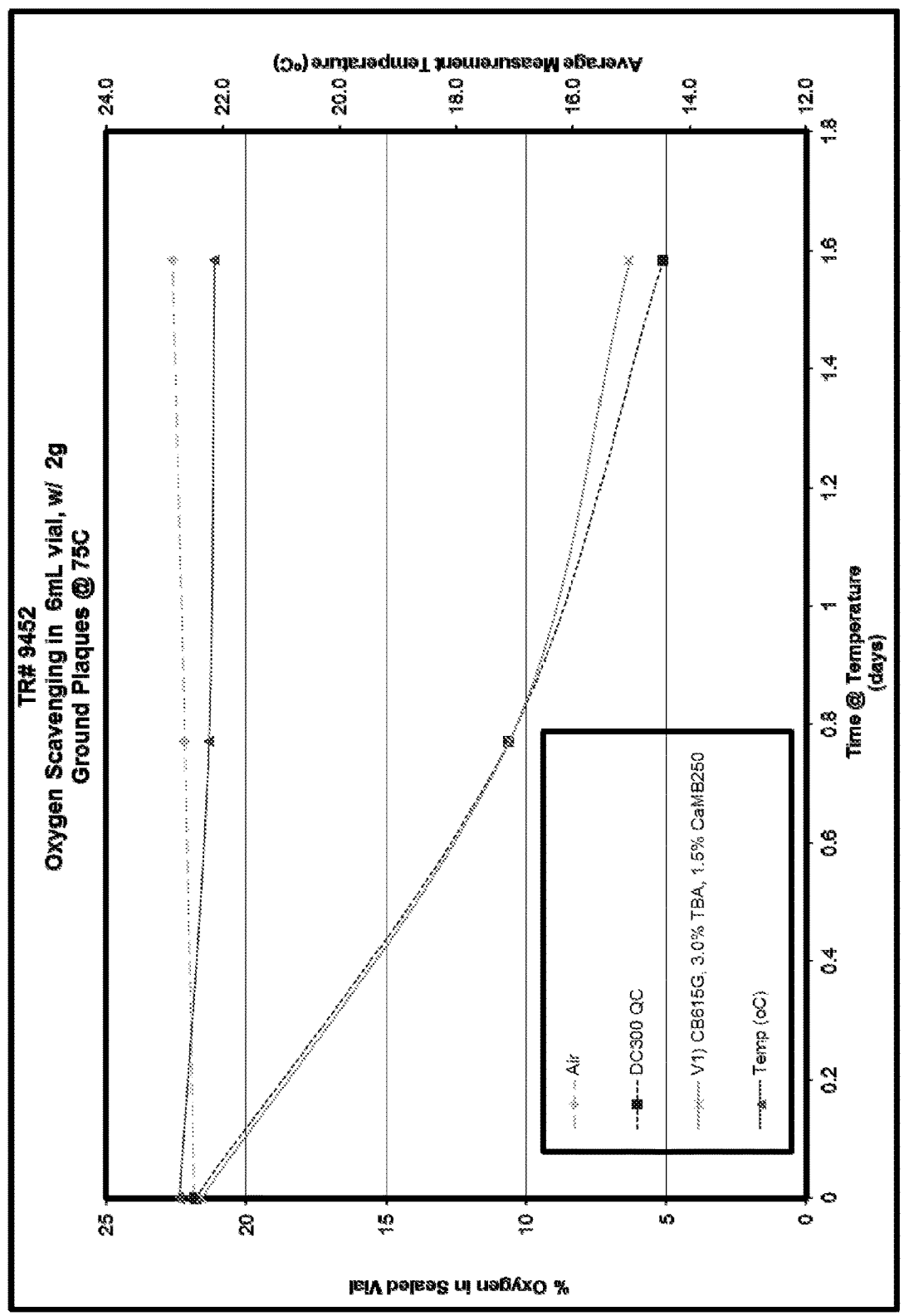
FIG. 2 shows a graph depicting oxygen scavenging data at 75° C. for plaques comprising a representative oxygen scavenger according to the present invention.

Polymer formulations comprising the compound prepared in Example 1 [benzene-1,3-diylbis(N,N-dibenzylmethanamine), or TBA] were prepared to evaluate oxygen scavenging performance. Polyethylene terephthalate (PET, CB651G) resin was mixed with 3% TBA, along with three different catalysts, (V1) 1.5% of catalyst masterbatch CaMB250 (containing 80 ppm of Co metal in the final formulation), (V2) 100 ppm (calculated as Co) of Cobalt neodecanoate powder, and (V3) 100 ppm (calculated as Co) of Cobalt acetate powder. Plaques formed from the representative polymer formulation plaques were compared to plaques formed from a control formulation using Constar International DC-300 oxygen scavenger (DC300 QC), which is a ground preform containing 1.4% of DC-300 and 1.5% of CaMB250. As seen from the data of FIGS. 1 and 2, all of the representative formulations exhibit significant oxygen scavenging ability at both 40° C. and 75° C., which is comparable to the oxygen scavenging performance of DC300 QC. As shown in FIG. 1, representative formulation V1 exhibits significantly better oxygen scavenging performance than the control formulation DC300 QC at 40° C. As shown in FIG. 2, a similar trend in oxygen scavenging performance can be seen at the higher test temperature of 75° C.

3. Example 2: Oxygen Scavenging Performance of TBA in Various Resins (TR9471):

In this Example, bottles were made via a standard two-stage injection molding process from several representative polymer formulations comprising TBA and various resins, along with two comparative polymer formulations comprising DC300. The representative and comparative formulations were prepared according to the parameters provided in Table 1. Actual scavenger LDR inside the packaging was verified using elemental nitrogen analysis. The calculations used to determine the actual LDRs of TBA and DC300 listed in the table below presumes that all nitrogen exists in the packaging in non-degraded form. Any reference to scavenger LDR in the discussion below is to the nominal scavenger LDR of either 1.4% or 3% as listed below.

TABLE 1

| # | Resin | Scavenger | Scavenger LDR | Catalyst and LDR | N conc. by EA (%) | Actual LDR (%) DC300 | Actual LDR (%) TBA |
|---|-------|-----------|------|-----|------|------|------|
| C1 | PS7000 | DC300 | 1.4% | CaMB250, 1.5% | 0.0689 | 0.9 | |
| V2 | PS7000 | TBA | 1.4% | CaMB250, 1.5% | 0.0602 | | 1.23 |
| V3 | CF746A | TBA | 1.4% | CaMB250, 1.5% | 0.0669 | | 1.37 |
| C4 | PS7000 | DC300 | 3% | CaMB250, 1.5% | 0.227 | 3 | |
| V5 | PS7000 | TBA | 3% | CaMB250, 1.5% | 0.128 | — | 2.6 |
| V6 | CF746A | TBA | 3% | CaMB250, 1.5% | 0.101 | | 2.1 |
| V8 | Ti818 | TBA | 3% | CaMB250, 1.5% | 0.114 | | 2.3 |

Parastar 7000 (PS7000), HeatWave (CF746A) and Laser + HS Ti818 (Ti818) are commercially available PET resin available from DAK America, Chadds Ford, PA, USA.

Figure 3:
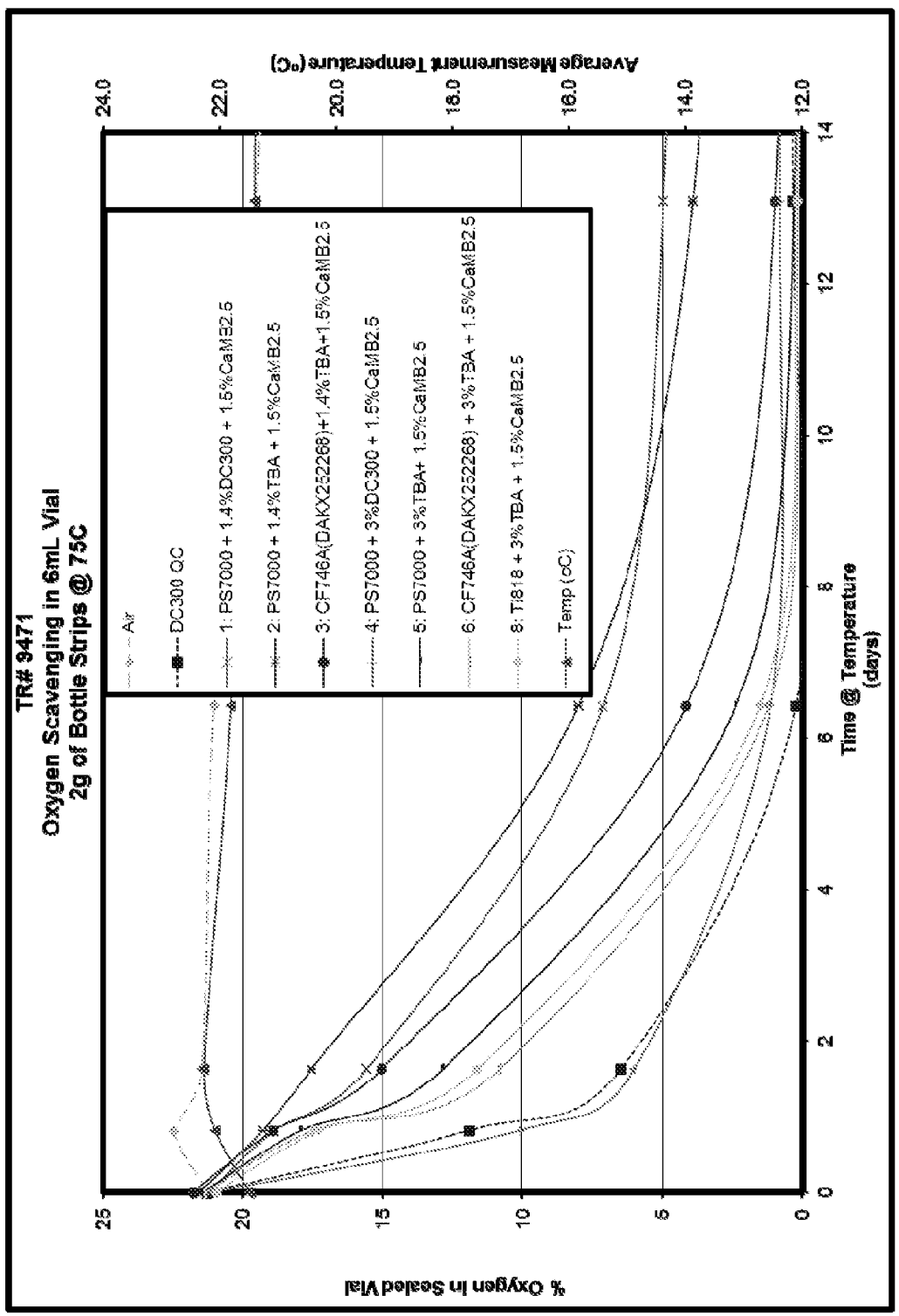
FIG. 3 shows a graph depicting oxygen scavenging data at 75° C. for bottle stripes comprising a representative oxygen scavenger according to the present invention.

As shown by the data in FIG. 3, at 75° C., all representative formulations containing TBA show reactivity immediately without an induction period. Notably, data from representative formulations V6 and V8 demonstrate TBA functions equally well in Ti818 resin and in CF746A resin, which are resins DC300 is not known to function well in. Without wishing to be bound by a particular theory, the data indicates that this new oxygen scavenger may have additional advantages over other previous scavengers with respect to resin compatibilities.

Figure 4:
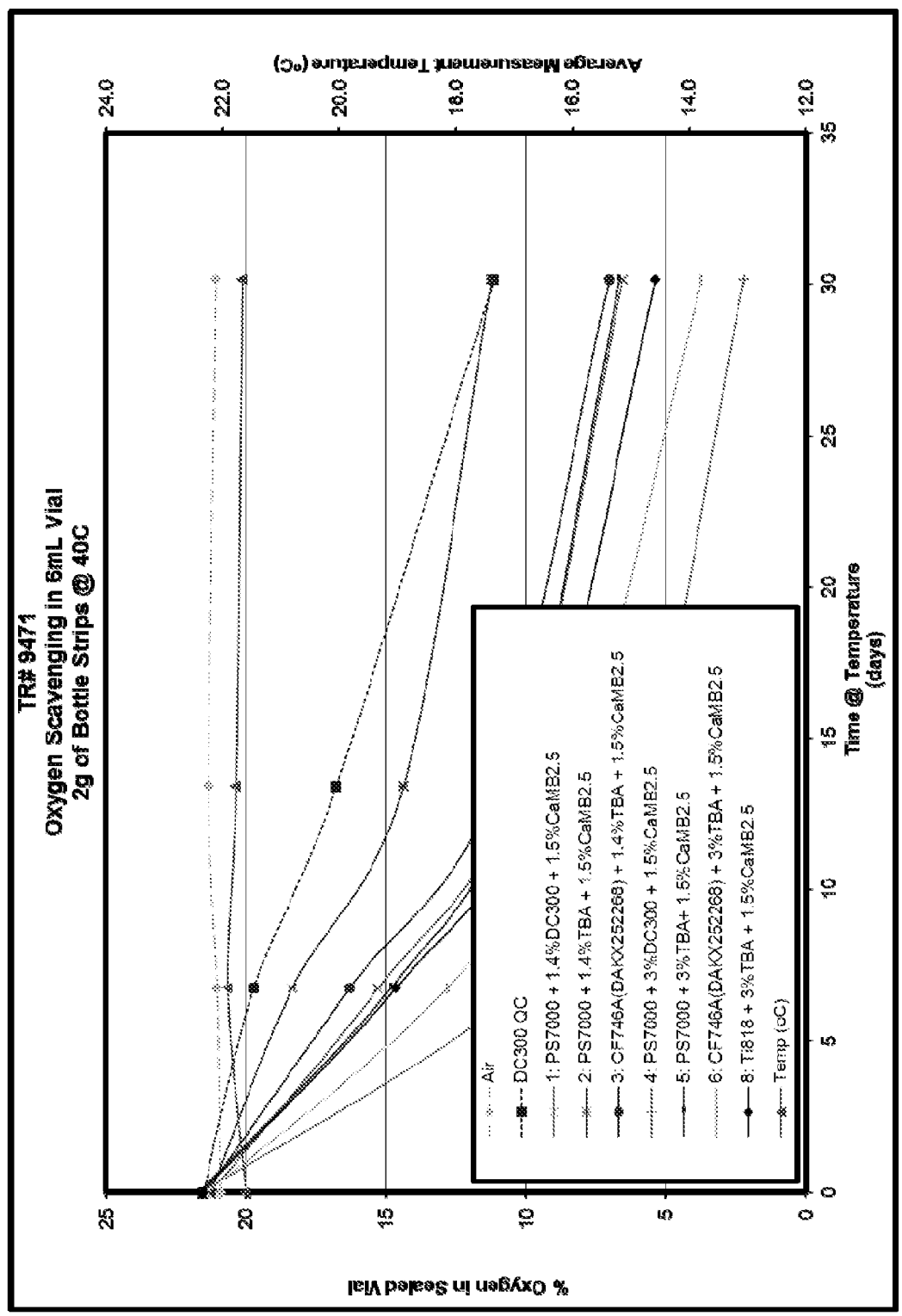
FIG. 4 shows a graph depicting oxygen scavenging data at 40° C. for bottle stripes comprising a representative oxygen scavenger according to the present invention.

As seen in FIG. 4, all of the representative formulations according to the present disclosure exhibit substantial oxygen scavenging ability at 40° C. While the 40° C. data shows that TBA has slightly less efficiency than the same amount of DC300, the TBA formulations function without a significant induction period. Although 3% TBA shows less activity in Ti818 than other resins, it should be noted that its performance was superior to the 1.4% DC300 formulation that was utilizes the more compatible PS7000 resin. Without wishing to be bound by a particular theory, this data is consistent with the 75° C. data, indicating that TBA has less resin compatibility issues than DC300.

IlliOp™ testing was then performed on the samples to confirm the Oxysense™ data. Briefly, IlliOp™ testing detects the amount of oxygen permeated through the bottle wall in real time. The tests involve mounting the bottle onto a brass plate with glue so as to form a closed system, with the exception of an in-pipe with N2 carrier gas and an out-pipe that connects to a detector. As $O_2$ permeates through the bottle wall, it is carried by the $N_2$ flow to the detector, which records the values in real time for use in calculating ingress rate. The IlliOp™ data is shown in Table 2 below.

TABLE 2

| Test # | Sample Composition | Equilibrium $O_2$ Ingress Rate [mL/ pkg/day] | Equilibrium $O_2$ Ingress Rate [ppm/ pkg/day]* | $O_2$ Ingress Over 180 Days |
|---|---|---|---|---|
| 1 | PS7000 + 1.4% DC300 + 1.5% CaMB2.5 (Control) | 0.0032 | 0.0077 | 1.3912 |
| 2 | PS7000 + 1.4% TBA + 1.5% CaMB2.5 | 0.0068 | 0.0164 | 2.9563 |
| 3 | CF746A + 1.4% TBA + 1.5% CaMB2.5 | 0.0062 | 0.0150 | 2.6955 |
| 4 | PS7000 + 3% DC300 + 1.5% CaMB2.5 | 0.0017 | 0.0041 | 0.7394 |
| 5 | PS7000 + 3% TBA + 1.5% CaMB2.5 | 0.0004 | 0.0010 | 0.1749 |
| 6 | CF746A + 3% TBA + 1.5% CaMB2.5 | 0.0004 | 0.0010 | 0.1749 |
| 8 | Ti818 + 3% TBA + 1.5% CaMB2.5 | 0.0071 | 0.0071 | 3.1210 |

Consistent with OxySense data, the IlliOp data show that 1.4% TBA gives 0.0065 ppm/pkg/day at equilibrium, which is on the same order of magnitude as compared to 1.4% DC300, whereas an increased LDR gave enhanced performance. 3% TBA reliably gives 0.0004 ppm/pkg/day permeation rate in CF746A and PS7000, lower than 3% DC300 reference. In Ti818, 3% TBA functions with rate of 0.0071 ppm/pkg/day, which is significantly better than DC300, which suggests that TBA has better resin compatibility.

The overall oxygen scavenging performance of TBA is comparable to DC300. In the compatible resins, even low LDRs of 1.4% TBA are satisfactory for applications that tolerate 3 ppm of $O_2$ ingression over a 6-month shelf life. However, at higher LDRs, not only does TBA oxygen scavenging performance greatly enhance, TBA does not exhibit resin compatibility problems seen in other oxygen scavenger at higher LDRs.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A composition comprising:
   a. a base polymer;
   b. at least one compound of formula

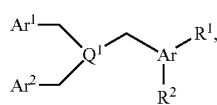
(I)

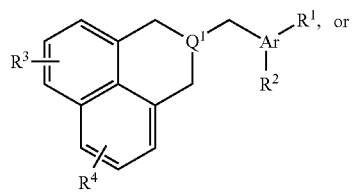
(II), or

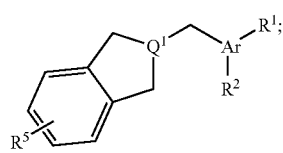
(III)

wherein Ar is aryl or heteroaryl;
wherein each $Q^1$ is independently N or P;
wherein each of $Ar^1$ and $Ar^2$ is independently aryl or heteroaryl; and wherein each $Ar^1$ and $Ar^2$ is independently substituted with 0, 1, 2, or 3 groups independently selected from halogen, C1-C4 alkyl, and electron withdrawing groups, and valence is satisfied;
wherein each of $R^1$ and $R^2$ is independently selected from hydrogen,

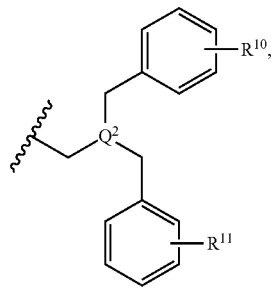

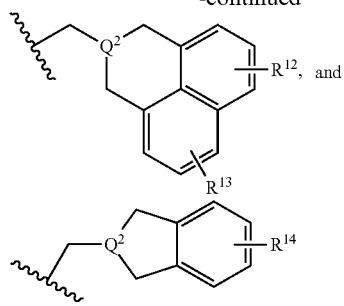

wherein $R^3$ represents three groups, each group independently selected from hydrogen, halogen, C1-C4 alkyl, and electron withdrawing groups;
wherein $R^4$ represents three groups, each group independently selected from hydrogen, halogen, C1-C4 alkyl, and electron withdrawing groups;
wherein $R^5$ represents four groups, each group independently selected from hydrogen, halogen, C1-C4 alkyl, and electron withdrawing groups;
wherein $R^{10}$ represents five groups independently selected from hydrogen, halogen, C1-C4 alkyl, and electron withdrawing groups;
wherein $R^{11}$ represents five groups independently selected from hydrogen, halogen, C1-C4 alkyl, and electron withdrawing groups;
wherein $R^{12}$ represents three groups independently selected from hydrogen, halogen, C1-C4 alkyl, and electron withdrawing groups;
wherein $R^{13}$ represents three groups independently selected from hydrogen, halogen, C1-C4 alkyl, and electron withdrawing groups;
wherein $R^{14}$ represents four groups independently selected from hydrogen, halogen, C1-C4 alkyl, and electron withdrawing groups; and
wherein each $Q^2$ is independently N or P; and
   c. cobalt in a positive oxidation state;
wherein said compound is present in an amount of about 0.10 to 10 weight percent of said composition, and
wherein cobalt is present as a salt having an anion selected from chloride, acetate, oleate, stearate, palmitate, 2-ethylhexanoate, neodecanoate, octanoate, lactate, naphthalate, malate, acetylacetonate, linoleate, and ethylene glycolate.

2. The composition of claim 1, wherein Ar is aryl selected from

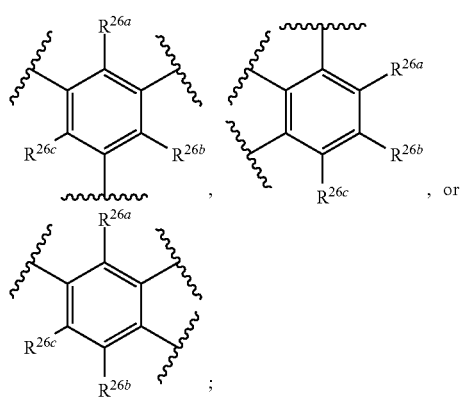

wherein each $R^{26a}$, $R^{26b}$, and $R^{26c}$ is independently selected from hydrogen, halogen, C1-C4 alkyl, and electron withdrawing groups.

3. The composition of claim 1, wherein cobalt is present in the composition in an amount of 10 to 400 ppm.

4. The composition of claim 1, wherein the base polymer comprises a polyester polymer.

5. The composition of claim 1, wherein the compound has the structure

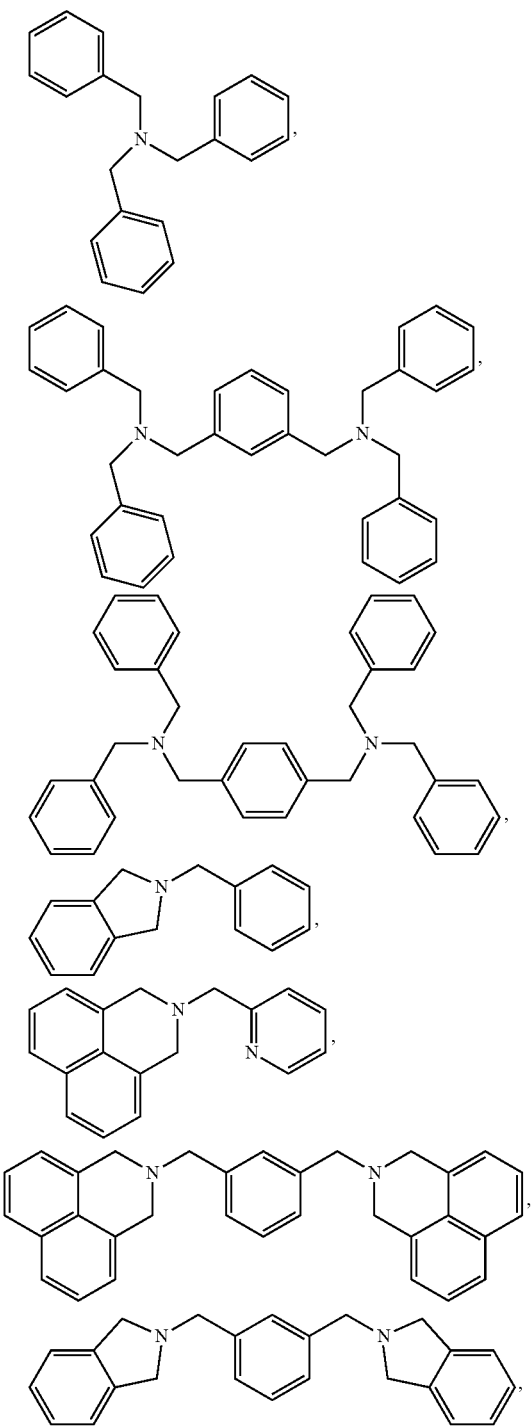

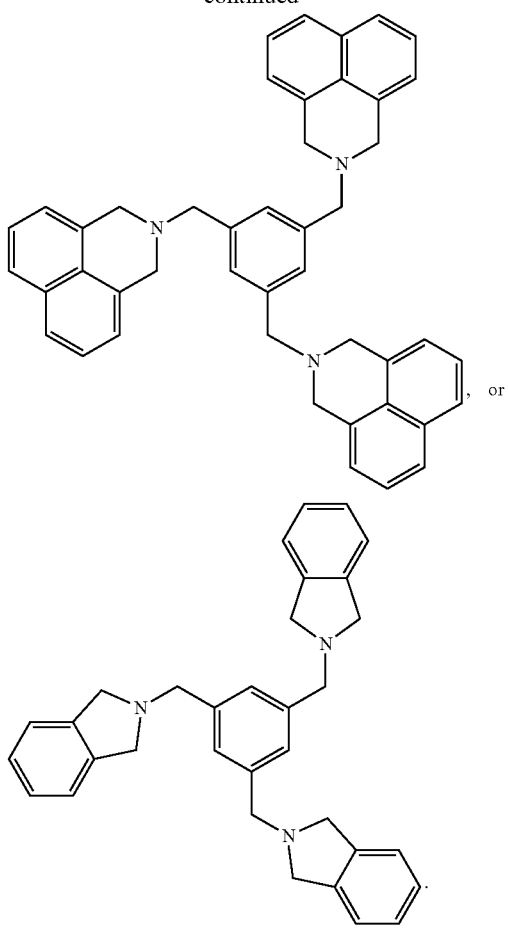

6. A composition comprising:
a. a base polymer;
b. at least one compound of formula

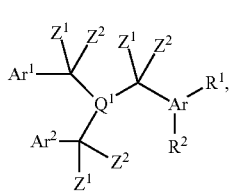

(VI)

wherein Ar is aryl or heteroaryl;

wherein each $Q^1$ is independently N or P;

wherein each of $Ar^1$ and $Ar^2$ is independently aryl or heteroaryl; and wherein each $Ar^1$ and $Ar^2$ is independently substituted with 0, 1, 2, or 3 groups independently selected from halogen, C1-C4 alkyl, and electron withdrawing groups, and valence is satisfied;

wherein each $Z^1$ and $Z^2$ are independently hydrogen, halogen, C1-C4 alkyl, electronic withdrawing group, electronic donating group, or collectively =O; provided that at least one set of $Z^1$ and $Z^2$ are hydrogens;

wherein each of R¹ and R² is independently selected from hydrogen,

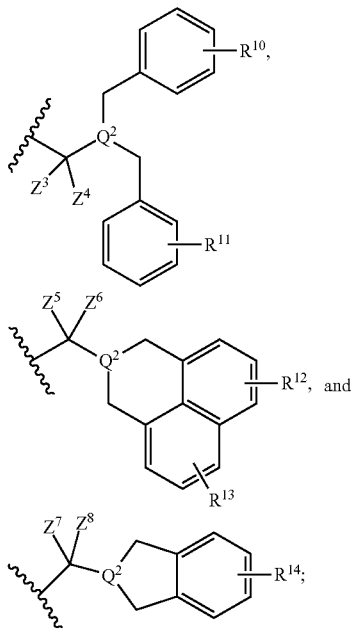

wherein R¹⁰ represents five groups independently selected from hydrogen, halogen, C1-C4 alkyl, and electron withdrawing groups;
wherein R¹¹ represents five groups independently selected from hydrogen, halogen, C1-C4 alkyl, and electron withdrawing groups;
wherein R¹² represents three groups independently selected from hydrogen, halogen, C1-C4 alkyl, and electron withdrawing groups;
wherein R¹³ represents three groups independently selected from hydrogen, halogen, C1-C4 alkyl, and electron withdrawing groups;
wherein R¹⁴ presents four groups independently selected from hydrogen, halogen, C1-C4 alkyl, and electron withdrawing groups;
wherein each Q² is independently N or P;
wherein each Z³ and Z⁴ are independently hydrogen, halogen, C1-C4 alkyl, electronic withdrawing group, electronic donating group, or collectively =O;
wherein each Z⁵ and Z⁶ are independently hydrogen, halogen, C1-C4 alkyl, electronic withdrawing group, electronic donating group, or collectively =O; and
wherein each Z⁷ and Z⁸ are independently hydrogen, halogen, C1-C4 alkyl, electronic withdrawing group, electronic donating group, or collectively =O; and
c. cobalt in a positive oxidation state;
wherein said compound is present in an amount of about 0.10 to 10 weight percent of said composition, and
wherein cobalt is present as a salt having an anion selected from chloride, acetate, oleate, stearate, palmitate, 2-ethylhexanoate, neodecanoate, octanoate, lactate, naphthalate, malate, acetylacetonate, linoleate, and ethylene glycolate.

7. An article of manufacture comprising a composition according to claim 1.

8. The article of claim 7, wherein the article is a preform, sheet, bottle, cup, or jar.

9. A wall for a package comprising a composition, said wall comprising:
a. one or more outer layers; and
b. one or more inner layers;
wherein at least one of said inner or at least one of said outer layers comprises a composition according to claim 1.

10. The wall of claim 9, wherein the first layer is disposed radially outward from said second layer.

11. A container from a film-forming polymer, having at least one wall comprising an effective amount of an oxygen-scavenging composition according to claim 1.

12. The composition of claim 1, wherein the compound has the formula:

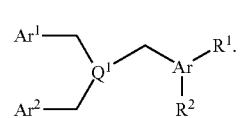

(I)

13. The composition of claim 12, wherein Ar is aryl, Ar¹ is aryl, Ar² is aryl, R¹ is hydrogen, and R² is:

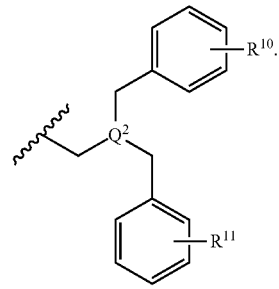

14. The composition of claim 1, wherein cobalt is cobalt (II) 2-ethylhexanoate, cobalt oleate, or cobalt (II) neodecanoate.

15. The composition of claim 6, wherein cobalt is in the +3 oxidation state.

16. The composition of claim 6, wherein cobalt is cobalt (II) 2-ethylhexanoate, cobalt oleate, or cobalt (II) neodecanoate.

17. The composition of claim 1, wherein cobalt is in the +3 oxidation state.

18. A composition comprising:
a. a polyester;
b. at least one compound of formula

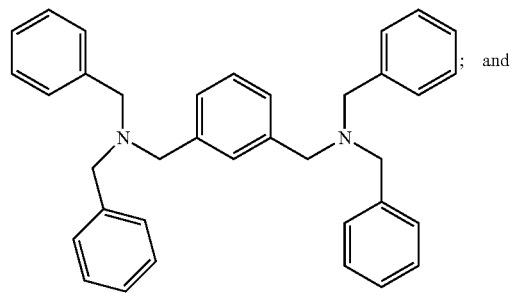 [SMILES: c1ccc(CN(Cc2ccccc2)Cc2cccc(CN(Cc3ccccc3)Cc3ccccc3)c2)cc1]

; and c. cobalt (II) 2-ethylhexanoate, cobalt oleate, cobalt (II) neodecanoate, or a mixture thereof;
wherein said compound is present in an amount of about 0.10 to 10 weight percent of said composition.

* * * * *